US012792926B2

(12) United States Patent
Sadilek

(10) Patent No.: US 12,792,926 B2
(45) Date of Patent: Nov. 10, 2026

(54) MAINTAINING PRIVACY DURING ATTRIBUTION OF A CONDITION

(71) Applicant: Google LLC, Mountain View, CA (US)

(72) Inventor: Adam Sadilek, Redmond, WA (US)

(73) Assignee: GOOGLE LLC, Mountain View, CA (US)

( * ) Notice: Subject to any disclaimer, the term of this patent is extended or adjusted under 35 U.S.C. 154(b) by 1192 days.

(21) Appl. No.: 17/772,883

(22) PCT Filed: Oct. 28, 2019

(86) PCT No.: PCT/US2019/058303

§ 371 (c)(1),
(2) Date: Apr. 28, 2022

(87) PCT Pub. No.: WO2021/086305

PCT Pub. Date: May 6, 2021

(65) Prior Publication Data

US 2022/0351057 A1 Nov. 3, 2022

(51) Int. Cl.
*G06N 3/098* (2023.01)
*G06F 16/2458* (2019.01)
(Continued)

(52) U.S. Cl.
CPC ......... *G06N 3/098* (2023.01); *G06F 16/2477* (2019.01); *G06F 21/6218* (2013.01);
(Continued)

(58) Field of Classification Search
CPC .......... G06N 5/04; G06N 20/00; G06N 3/098; G06F 16/2477; G06F 21/6218; G06F 2221/2111; G06F 2221/211; G16H 50/80
See application file for complete search history.

(56) References Cited

U.S. PATENT DOCUMENTS

| | | | | |
|---|---|---|---|---|
| 6,009,163 | A | 12/1999 | Nabkel et al. | |
| 8,049,614 | B2 * | 11/2011 | Kahn | G16H 50/80 340/521 |

(Continued)

FOREIGN PATENT DOCUMENTS

| | | |
|---|---|---|
| EP | 3108393 | 12/2016 |
| WO | WO 2018/093462 | 5/2018 |

(Continued)

OTHER PUBLICATIONS

International Search Report and Written Opinion for Application No. PCT/US2019/058303, mailed Jul. 23, 2020, 14 pages.

(Continued)

*Primary Examiner* — Andrew T Chiusano
(74) *Attorney, Agent, or Firm* — DORITY & MANNING, P.A.

(57) ABSTRACT

Predictive modeling using statistical evaluation combined with federated learning is described to enable incident map creation while preserving anonymity and achieving fine granularity. Machine-learned models (116) are trained to infer when persons associated with individual user devices (102) do or do not have a condition. The models (116) are deployed to the user devices (102) and return generalized location data and aggregated statistics about inferences made by the models. A remote system collects the aggregated statistics (120) and builds an incidence map (122-1, 122-2) identifying hotspots and coldspots for the condition. The incidence map identifies affected regions, with fine granularity down to a neighborhood or street level. The subregion-level information is regularly updated as new inferences, and new aggregated statistics, are made. Hence, the incidence map (122-1, 122-2) is current and highly detailed.

15 Claims, 13 Drawing Sheets

(51) Int. Cl.
*G06F 21/62* (2013.01)
*G06N 5/04* (2023.01)
*G06N 20/00* (2019.01)
*G16H 50/80* (2018.01)

(52) U.S. Cl.
CPC ............. *G06N 20/00* (2019.01); *G16H 50/80* (2018.01); *G06F 2221/2111* (2013.01); *G06N 5/04* (2013.01)

(56) References Cited

U.S. PATENT DOCUMENTS

| | | | | |
|---|---|---|---|---|
| 8,090,592 | B1 | 1/2012 | Goodall et al. | |
| 8,365,075 | B2 | 1/2013 | Bhogal et al. | |
| 10,318,875 | B2 | 6/2019 | Avegliano et al. | |
| 10,366,791 | B1 | 7/2019 | Thiagarajan | |
| 10,990,850 | B1 * | 4/2021 | Chen | G06V 10/7747 |
| 12,154,692 | B2 * | 11/2024 | Sadilek | G06N 20/00 |
| 2003/0187615 | A1 * | 10/2003 | Epler | G16H 40/20 702/181 |
| 2008/0055096 | A1 | 3/2008 | Aylward | |
| 2010/0175006 | A1 | 7/2010 | Li | |
| 2010/0274573 | A1 | 10/2010 | Feied et al. | |
| 2011/0295776 | A1 | 12/2011 | Donato et al. | |
| 2012/0005132 | A1 | 1/2012 | Horvitz et al. | |
| 2012/0005224 | A1 | 1/2012 | Ahrens et al. | |
| 2012/0042022 | A1 | 2/2012 | Sheth et al. | |
| 2012/0256745 | A1 | 10/2012 | Piett et al. | |
| 2014/0129544 | A1 | 5/2014 | Haugen et al. | |
| 2014/0236613 | A1 | 8/2014 | McMillan et al. | |
| 2015/0170296 | A1 | 6/2015 | Kautz et al. | |
| 2016/0034712 | A1 | 2/2016 | Patton et al. | |
| 2016/0135755 | A1 | 5/2016 | Lu et al. | |
| 2016/0267238 | A1 * | 9/2016 | Nag | G16H 10/60 |
| 2017/0161614 | A1 | 6/2017 | Mehta et al. | |
| 2017/0308678 | A1 | 10/2017 | Apreleva et al. | |
| 2017/0310605 | A1 | 10/2017 | Garcia et al. | |
| 2018/0181878 | A1 * | 6/2018 | Kasiviswanathan | G06F 21/6245 |
| 2018/0316502 | A1 * | 11/2018 | Nadeau | H04L 9/085 |
| 2019/0148023 | A1 * | 5/2019 | Sadilek | G06N 3/044 705/2 |
| 2019/0252078 | A1 * | 8/2019 | Schubert | G06N 3/044 |
| 2019/0372859 | A1 * | 12/2019 | Mermoud | H04L 41/28 |
| 2022/0171874 | A1 * | 6/2022 | Lundbæk | G06N 20/00 |
| 2023/0267375 | A1 | 8/2023 | Szeto et al. | |

FOREIGN PATENT DOCUMENTS

| | | | | |
|---|---|---|---|---|
| WO | WO 2018/093462 A1 | 5/2018 | | |
| WO | WO-2021189105 A1 * | 9/2021 | | G16H 50/80 |

OTHER PUBLICATIONS

Metzger et al., "The use of regional platforms for managing electronic health records for the production of regional public health indicators in France", BMC Medical Informatics and Decision Making, Dec. 28, 2012, https://doi.org/10.1186/1472-6947-12-28, 14 pages.
Allen et al., "The Effect of Forest Fragmentation on Lyme Disease Risk", Conservation Biology, vol. 17, No. 1, 2003, 10 pages.
Arendt et al., "Reporting of Foodborne Illness by U.S. Consumers and Healthcare Professionals", International Journal of Environmental Research and Public Health, vol. 10, No. 8, 2013, pp. 3684-3714.
Bacon et al., "Surveillance for Lyme Disease—United States, 1992-2006", Department of Health & Human Services, Centers for Disease Control and Prevention, Atlanta, Georgia, United States Oct. 3, 2008, 16 pages.
Brown et al., "Role of Serology in the Diagnosis of Lyme Disease", Jama, vol. 282, No. 1, Jul. 7, 1999, pp. 62-66.
Brownstein et al., "A Climate-Based Model Predicts the Spatial Distribution of the Lyme Disease Vector Lxodes Scapularis in the United States", Environmental Health Perspectives, vol. 111, No. 9, 2003, pp. 1152-1157.
Brownstein et al., "Empirical Evidence for the Effect of Airline Travel on Inter-Regional Influenza Spread in the United States", PLoS Med., Sep. 3, 2006, 10 pages.
Centers for Disease Control and Prevention, "About FoodNet", https://cdc.gov/foodnet/about.html, retrieved on Jan. 11, 2018, 2 pages.
Centers for Disease Control and Prevention, "Beliefs that Restaurant Meals Made People Sick", https://www.cdc.gov/nceh/ehs/ehsnet/plain_language/beliefs-restaurant-meals-made-people-sick.htm, retrieved on Jan. 11, 2018, 2 pages.
Centers for Disease Control and Prevention, "Effect of Electronic Laboratory Reporting on the Burden of Lyme Disease Surveillance—New Jersey, 2001-2006", Morbidity and Mortality Weekly Report, vol. 57, No. 2, 2008, 7 pages.
Centers for Disease Control and Prevention, "Lyme Disease Surveillance and Available Data", www.cdc.gov/lyme/stats/survfaq.html , Nov. 13, 2017, retrieved on Jan. 11, 2018, 1 page.
Cook et al., Assessing Google Flu Trends Performance in the United States during the 2009 Influenza Virus A (H1N1) Pandemic, PLoS One, vol. 6, No. 8, Aug. 2011, 8 pages.
Food Safety, "Winnable Battles", https://www.cdc.gov/winnablebattles/foodsafety/, retrieved on Jan. 11, 2018, 2 pages.
Gabrilovich et al., "Classifying Search Queries Using the Web as a Source of Knowledge", Association of Computing Machinery Transactions on the Web, New York, New York, 2009, 28 pages.
Ginsberg et al., "Detecting Influenza Epidemics Using Search Engine Query Data" Nature 457, 2009, pp. 1012-1014.
Golder, "Diurnal and Seasonal Mood Vary with Work, Sleep, and Daylength Across Diverse Cultures", Science, vol. 333 Sep. 30, 2011, pp. 1878-1881.
Google Patents Search, Mar. 10, 2020.
Google Patents Search, Sep. 16, 2020.
Disease Prediction System using Open Data (EP 3108393A1).
Gould et al., "Knowledge, Attitudes, and Behaviors Regarding Lyme Disease Prevention Among Connecticut Residents, 1999-2004", Vector-Borne and Zoonotic Diseases, vol. 8, No. 6, 2008, pp. 769-776.
Grassly et al., "Host Immunity and Synchronized Epidemics of Syphilis Across the United States", Letters to Nature, Jan. 27, 2005, pp. 417-421.
Harris et al., "Health Department Use of Social Media to Identify Foodborne Illness", Centers for Disease Control and Prevention Morbidity and Mortality Weekly Report, Chicago, Illinois, United States Aug. 15, 2014, pp. 681-716.
Harris et al., "Using Twitter to Identify and Respond to Food Poisoning: The Food Safety STL Project", Journal of Public Health Management and Practice, vol. 23, No. 6, Nov./Dec. 2017, pp. 577-580.
Hswen et al., "Use of a Digital Health Application for Influenza Surveillance in China", American Journal of Public Health, vol. 107, No. 7, Jul. 7, 2017, pp. 1130-1136.
International Preliminary Report on Patentability for PCT/US2019/058303, mailed on May 12, 2022, 7 pages.
Kilpatrick et al., "Drivers, Dynamics, and Control of Emerging Vector-Borne Zoonotic Diseases", The Lancet, vol. 380, Issue 9857, Dec. 1, 2012, pp. 1946-1955.
Kitzinger, Qualitative Research. Introducing Focus Groups, The BMJ, vol. 311, Issue 7000, Jul. 29, 1995, pp. 299-301.
Langsrud, "ANOVA for Unbalanced Data: Use Type II instead of Type III Sums of Squares", Statistics and Computing, vol. 13, No. 2, Apr. 2003, pp. 163-167.
Lim et al., "An Unsupervised Machine Learning Model for Discovering Latent Infectious Diseases Using Social Media Data", Department of Industrial and Manufacturing Engineering, The Pennsylvania State University, Journal of Biomedical Informatics, Dec. 26, 2016, 13 pages.
Metzger et al., "The use of regional platforms for managing electronic health records for the production of regional public health indicators in France", Apr. 3, 2012, 14 pages.

(56) References Cited

OTHER PUBLICATIONS

Ogden et al., “Active and Passive Surveillance and Phylogenetic Analysis of Borrelia Burgdorferi Elucidate the Process of Lime Disease Risk Emergence in Canada”, Environmental Health Perspectives, vol. 118, No. 7, 2010, pp. 909-914.

Ostfeld et al., “Climate, Deer, Rodents, and Acorns as Determinants of Variation in Lyme-Disease Risk”, vol. 4, No. 6, May 9, 2006, pp. 1058-1068.

Sadilek et al., “Deploying nEmesis: Preventing Foodborne Illness by Data Mining Social Media”, 28$^{th}$ Association of the Advancement of Artificial Intelligence Conference on Innovative Applications, Phoenix, Arizona, United States, Feb. 13-16, pp. 3982-3989.

Scharff, “Economic Burden from Health Losses Due to Foodborne Illness in the United States”, Journal of Food Protection, vol. 75, No. 1, 2012, pp. 123-131.

Schauber et al., “What is the Best Predictor of Annual Lyme Disease Incidence: Weather, Mice, or Acorns?”, Ecological Applications, vol. 15, No. 2, 2005, pp. 575-586.

Shah et al., “Use of Internet Search Data to Monitor Rotavirus Vaccine Impact in the United States, United Kingdom, and Mexico”, Journal of the Pediatric Infectious Diseases Society, Mar. 21, 2017, 8 pages.

Singhal, “Introducing the Knowledge Graph: Things, not Strings” 2012, https://googleblog.blogspot.com.au/2012/05/introducing-knowledge-graph-things-not.html, retrieved on May 16, 2012, 8 pages.

Stricker et al., “Lyme Disease: Call for a “Manhattan Project” to Combat the Epidemic”, Pathogens, vol. 10, No. 1, Jan. 2014, 3 pages.

Thornton, “Delivering Faster Results with Food Inspection Forecasting”, Data-Smart City Solutions, Ash Center at Harvard University, May 19, 2015, http://datasmart.ash.harvard.edu/news/article/delivering-faster-results-with-food-inspection-forecasting-631, retrieved on Jan. 11, 2018, 5 pages.

Volkow et al., “Adverse Health Effects of Marijuana Use”, Apr. 11, 2016, https://www.ncbi.nlm.nih.gov/pmc/articles/PMC4827335/, retrieved on Jan. 11, 2018, 12 pages.

Weinberger et al., “Feature Hashing for Large Scale Multitask Learning”, 26$^{th}$ Annual International Conference on Machine Learning, Montreal Quebec, Canada, Jun. 14-18, 2009, 8 pages.

Yang et al., “Using Electronic Health Records and Internet Search Information for Accurate Influenza Forecasting”, BMC Infectious Diseases, vol. 17, Issue 332, 2017, 9 pages.

Zhou et al., “Monitoring Epidemic Alert Levels by Analyzing Internet Search Volume”, Institute of Electrical and Electronics Engineers Transactions and Biomedical Engineering, vol. 60, No. 2, Feb. 2013, 7 pages.

Chinese Search Report Corresponding to Application No. 2019801032034 on Apr. 16, 2025.

* cited by examiner 800-2

800-3

MAINTAINING PRIVACY DURING ATTRIBUTION OF A CONDITION

PRIORITY CLAIM

This application is based upon and claims the right of priority under 35 U.S.C. § 371 to International Application No. PCT/US2019/058303 filed on Oct. 28, 2019, which is incorporated by reference herein.

BACKGROUND

Some machine-learned models are trained to predict health epidemics from signals mined from internet searches, social media, or other online data. While predicting health conditions may be useful, treatment and containment operations require precise knowledge of when and where infections occur. Unlike prediction, this validation of if and when the condition occurs requires feedback as to actual conditions on-the-ground. Various ways to validate health epidemics using ground truth data (e.g., country-level influenza data from a government agency) and online data (e.g., search and social media trends) have been considered. For example, health providers pool data about multiple people to make a predictive model for future risk adjustment. However, the existing sources of ground truth data needed to build such a predictive model are too coarse to be used to build a model for validation because the data is too old or inaccurate. Furthermore, online data is invariably indexed (and therefore skewed) to a certain region, making it less suitable for isolating and containing an outbreak that originates from a different region. Thus, current techniques rely on often inaccurate, non-recent, or skewed information, which leads to incomplete incidence map generation. This lack of accurate information limits the impact of vaccination strategies and efficacy of interventions performed.

To address limitations in the current techniques, more timely, on-device, or unskewed data may aid in providing superior incidence maps. While better data can aid in providing superior incidence map generation, better data is often unavailable due to privacy concerns.

SUMMARY

This disclosure describes systems and techniques for maintaining privacy during attribution of a condition, such as an occurrence of an infectious disease. Machine-learned models are trained (e.g., using self- and/or semi-supervised learning) based on noisily-labeled data leveraging multiple sensors or data streams locally on the device. For opted-in users, the trained models make inferences about whether a person has a particular condition, given signals the model extracts from inputted data. The input signals are partially independent (e.g., daily routine based on location and mobility, audio-based signals, text-based signals) and therefore can be statistically fused together to create learning and inference that outperforms any signal modeled alone. An inference indicates whether or not signals indicate a person (e.g., a user) associated with the user device has a particular condition. The models execute locally on user devices and generate inferences over multiple intervals. Each model outputs information about the inferences to a remote system that generates incidence maps and/or applies the information in other ways. Rather than output information indicating actual inferences made by the model, however, the user device protects user privacy. The user device aggregates statistics computed about the actual inferences and shares the aggregated statistics with the remote system instead. The statistics, for example, indicate a frequency at which a condition is inferred within a specific unit of time and a specific unit of geographical area. The user devices inject "strategic noise" into the statistics before transmission to the remote system as a way to further promote privacy; the noise prevents backward traceability to the user devices. These, as well as other techniques, may be used to pretreat the aggregated statistics and remove any personally identifiable information before transmission to the remote system.

Based on aggregated statistics collected from multiple user devices and models, the remote system builds an incidence map for the geographic region. The remote system divides the incidence map into small subregions. For each subregion, inferences about the condition can be made either from actual statistics collected for that subregion or based on predictions made from the actual statistics collected for neighboring subregions. The remote system generates each incidence map from subregion or very low level (e.g., neighborhood or street view) data and, therefore, the incidence map captures the rate of incidence for a particular condition, down to the subregion or low level. The remote system regularly updates the incidence map as additional aggregated statistics come in from other devices in response to inferences being made by the local models. Hence, the incidence map is current, even if some of the data that trains the model is old. The incidence maps have fine granularity and detail across multiple subregions and can remain current instead of being tied to delayed data-reporting cycles that would otherwise make mapping out a treatment and isolation plan for the condition impractical. With ongoing federated learning occurring on individual devices, more-timely, accurate, and unskewed data can be used to validate whether or not a subregion is affected by a condition, leading to accurate incidence map generation for enhancing the impact of vaccination strategies and efficacy of other interventions and treatments in affected geographic regions. Reliance on existing sources of ground truth data and online data is no longer necessary. With federated learning in a privacy-first environment, high-level and anonymized incidence maps outlining subregions affected by a condition can be created. The timeliness and better resolution of the inferences and maps enables stronger nowcasts, forecasts, and resulting interventions against diseases.

Throughout the disclosure, examples are described where a computing system (e.g., a user device, a remote system) analyzes information (e.g., received signals, online data, aggregated statistics) associated with a user or a user device. The computing system uses the information associated with the user after the computing system receives explicit permission from the user to collect, store, or analyze the information. For example, in situations discussed below in which a remote system analyzes aggregated statistics output from a user device in a particular geographic location, a user will be provided with an opportunity to control whether programs or features of the remote system or the user device can collect and make use of the aggregated statistics to maintain privacy during multi-modal on-device machine-learning (e.g., federated learning by multiple devices) and attribution of a condition. Individual users, therefore, have control over what the computing system can or cannot do with aggregated statistics or with other information associated with the user. Aggregated statistics or other information associated with a user is pre-treated in one or more ways so that personally identifiable information is removed before being transferred, stored, or otherwise used. For example, before a user device shares aggregated statistics with a remote system, the user device inserts noisy data into the aggregated statistics. Pre-treating the data this way ensures the aggregated statistics cannot be traced back to the user, and in the process, removes any personally identifiable information that would otherwise be inferable from the aggregated statistics. Thus, the user has control over whether information about the user is collected and, if collected, how such information may be used by the computing system.

In some aspects, a computer-implemented method is described for maintaining privacy during attribution of a condition (e.g., malaria, chikungunya, zika, dengue, ebola, other infectious diseases) for a geographic region. The method includes training, by a remote system, a machine-learned model to infer, based on signals received by a user device in the geographic region, whether a person associated with the user device has the condition. The method continues by deploying, by the remote system, copies of the machine-learned model for local execution at each of a group of user devices, and collecting, by the remote system and from the group of user devices, aggregated statistics of inferences made by the copies of the machine-learned model. The method further includes determining, by the remote system, based on the aggregated statistics, an incidence rate of the condition in a particular subregion of the geographic region. The method concludes with outputting, by the remote system, based on the incidence rate of the condition in the particular subregion, an incidence map of the geographic region indicating a different incidence rate between multiple subregions of the geographic region.

In other aspects, another computer-implemented method is described. The other method includes receiving, by a user device and from a remote system, a copy of a machine-learned model trained to infer, based on signals received by the user device while in a particular subregion of the geographic region, whether a person associated with the user device has the condition. The other method further includes inputting, to the machine-learned model, one or more of the signals received by the user device at two or more different intervals of time, and responsive to inputting the one or more of the signals, determining multiple inferences made by the machine-learned model as to whether the person associated with the user device has the condition. The other method continues by generating, by the user device, based on the multiple inferences made by the machine-learned model, aggregated statistics as to whether persons in a particular subregion have the condition. The other method concludes by outputting an indication of the aggregated statistics to a remote system that determines, based on the aggregated statistics, an incidence map of the geographic region indicating a different incidence rate between multiple subregions of the geographic region.

This document also describes computer-readable media having instructions for performing the above-summarized methods. Additional methods are set forth herein, as well as systems and means for performing the above-summarized and these additional methods.

This summary is provided to introduce simplified concepts for maintaining privacy during attribution of a condition, which is further described below in the Detailed Description and Drawings. This summary is not intended to identify essential features of the claimed subject matter, nor is it intended for use in determining the scope of the claimed subject matter.

BRIEF DESCRIPTION OF THE DRAWINGS

The details of one or more aspects of maintaining privacy attribution of a condition are described in this document with reference to the following drawings. The same numbers are used throughout the drawings to reference like features and components:

FIGS. 7-1 through 7-3 illustrate an example progression of an incidence map as a computing system collects aggregated statistics, over time.

FIGS. 8-1 through 8-4 illustrate an example of containing a condition based on incidence maps generated by a computing system that maintains privacy during multi-modal on-device machine-learning.

DETAILED DESCRIPTION

Figure 1:
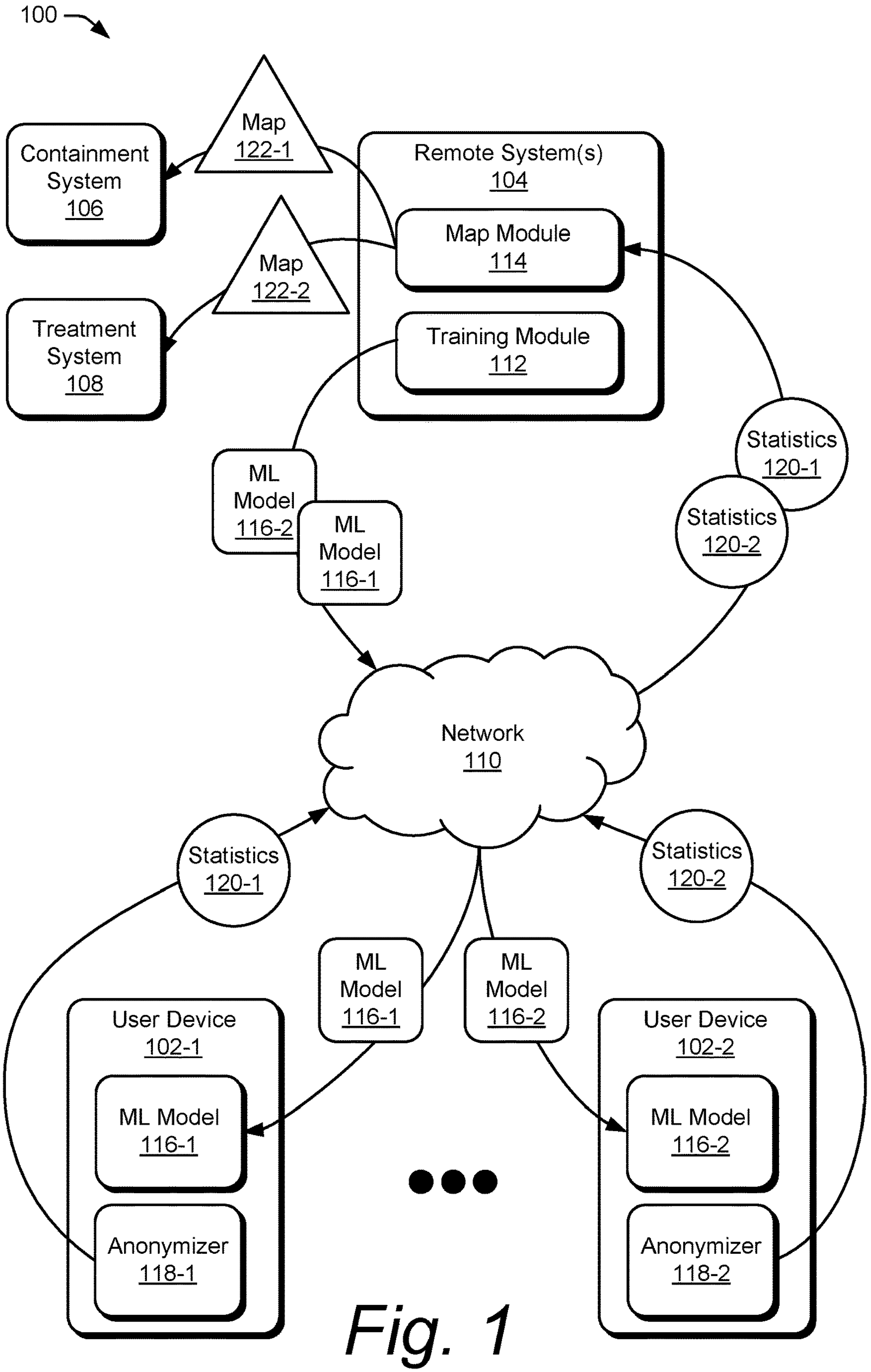
FIG. 1 illustrates an example environment in which techniques for maintaining privacy during multi-modal on-device machine-learning and attribution of a condition can be implemented.

This disclosure describes techniques and systems for maintaining privacy during attribution of a condition. By jointly modeling a collection of signals in a privacy-first way, the described techniques and systems enable accurate and personalized risk predictions for multiple different conditions, without letting personally identifiable information that has been collected locally and with informed consent, from leaving a person's user device. The described systems and techniques involve predictive modeling and statistical evaluation combined with federated (on-device) learning to create high-level and anonymized incidence maps with fine granularity and detail.

When it comes to predictive modeling, a machine-learned model is trained to predict conditions based on inferences made from ground truth data and indexed online data compiled over time. Evidence suggests that existing machine-learned models can feasibly predict an outbreak of a particular disease in a particular country using these existing data sources. On the other hand, validating an outbreak of infectious disease or other condition presents a different problem. Vaccination strategies and the efficacy of intervention treatments depend on identifying times and locations of occurrences of a condition, which requires a different data set, beyond traditional ground truth data and indexed-online data that is suitable for prediction.

For validating a condition, existing ground truth data is often too coarse (e.g., in that the data represents a country-level granularity) and is often too old (e.g., having been collected and reported over several months or years). Validation requires recent data collected at a neighborhood-level of granularity (e.g., a square meter, a hundred square meters) as opposed to a country-level of granularity (e.g., a square kilometer, ten square kilometers).

Existing online data may be more current than ground truth data, but the online data is invariably indexed (and therefore skewed) to a particular geographic region, typically a user's home district. Invariably indexed search and social media information may not be relevant for making inferences about a condition, particularly when the indexed search and social media information is generated by a user device receiving signals in a different region. For example, for a disease such as dengue, transmission often occurs during daytime due to bites from dengue-carrying mosquitoes. Transmission from a mosquito can occur while a patient is outside their home district, for example, when online data is generated from the person's search queries or social media interactions, such as, while the patient is working or traveling outside their home district. A discrepancy between the indexing of online data and the actual locations of users who are the cause of the online data can negatively impact the accuracy of risk maps and the efficacy of disease control programs that depend on such data. To overcome deficiencies with current machine-learned models and data sets, techniques, and systems for federated machine-learning by multiple devices and attribution of a condition are described.

The described systems and techniques enhance predictive modeling techniques using statistical evaluation combined with federated (on-device) learning. Such predictive modeling enables incident map creation with fine granularity and anonymity. Machine-learned models are trained to infer when persons associated with individual user devices do or do not have a condition or disease. The models are deployed to user devices from which the models return generalized location data and aggregated statistics about inferences made about the condition or disease. A remote system collects the aggregated statistics and builds an incidence map identifying hotspots and coldspots for the particular condition or disease. Statistical inferences are made for subregions that lack aggregated statistics. The incidence map indicates the rate of incidence, with fine granularity down to a neighborhood or street level. The subregion-level information is regularly updated as new inferences are made, and new aggregated statistics are collected. Hence, this enables the automated creation of incidence maps with fine granularity and anonymity.

The incidence maps can be output to application subscribers that use the maps as tools to combat current epidemics. The remote system automatically adapts the incidence maps to indicate changes in hotspots and coldspots of infected persons without having any information about user or device identities. Instead of explicitly modeling a health state of an entire geographic region, the remote system models the incidence rate in a given subregion and time interval. This has several advantages including a stronger privacy guarantee because of heavier aggregation earlier in the pipeline (e.g., before transmission to the remote system), increased coverage because of fewer obstacles to deployment through adaptive aggregation, and direct learning as opposed to learning from stale ground truth data (e.g., independent hospital statistics, public health research).

FIG. 1 illustrates an example environment 100 in which techniques for maintaining privacy during multi-modal on-device machine-learning and attribution of a condition can be implemented. The example environment 100 includes a group of user devices 102, including user device 102-1 through user device 102-2. The group of user devices 102 are in communication, through a network 110, with a remote system 104. The network 110 enables the remote system 104 to exchange data with the group of user devices 102. The remote system 104 can communicate with a containment system 106 and a treatment system 108 through the network 110 or through other communication channels.

The network 110 can be any wired or wireless network capable of exchanging data between remote devices and systems. For example, the network 110 may include an intranet or the internet. The network 110 includes typical hardware and software enabling wired or wireless transmission of communications (e.g., packets) between devices 102-1 and 102-2, and systems 104, 106, and 108, when connected to the network 110. The network 110 may be a cellular or WiFi™ network.

The user devices 102 (also sometimes referred to as computing devices or user equipment) may be any type of mobile or non-mobile computing device capable of receiving signals that are indicative of a particular condition. As a mobile computing device, the user devices 102 can be a mobile phone, a laptop computer, a wearable device (e.g., watches, eyeglasses, headphones, clothing), a tablet device, an automotive/vehicular device, a portable gaming device, an electronic reader device, or a remote-control device, or other mobile computing device capable of receiving online data or signals. As a non-mobile computing device, the user devices 102 may be a refrigerator, doorbell, thermostat, security system or control pad, a desktop computer, a television device, a display device, an entertainment set-top device, a streaming media device, a tabletop assistant device, a non-portable gaming device, business conferencing equipment, or other non-mobile computing device capable of receiving signals that help infer whether a user has a condition.

The remote system 104 provides incidence mapping services to application subscribers executing at the containment system 106 and the treatment system 108. A map module 114 generates incidence maps 122-1 and 122-2 (collectively "incidence maps 122"), as well as other maps of various conditions. The term "map" does not imply that incidence rate data is presented in a particular graphical format. In some implementations in accordance with the present disclosure, the incidence maps 122 may be a data structure (e.g., an array, object, or file) storing the incidence rate for each of a plurality of subregions of the geographic region. In other implementations, however, the incidence maps 122 may be a graphical representation of the geographic region, showing the incidence rates in multiple subregions. The map module 114 generates incidence maps by 1) compiling aggregated statistics collected for each subregion of a geographic region, and 2) inferring statistics for each subregion where the collected aggregated statistics are insufficient for statistical predictions. The aggregated statistics indicate presence or absence of the condition or ambiguity. The remote system 104 can work on any condition, and some examples include infectious diseases such as influenza, malaria, chikungunya, zika, ebola, or dengue. It will be appreciated these are purely non-limiting examples, and that the condition may be any infectious disease or other health risk. As another example, a condition may relate to exposure to an environmental factor, such as a chemical or a source of radiation. Although illustrated as a single computing system, the remote system 104 may include multiple computing systems.

To collect the statistics necessary to generate the incidence maps 122, the remote system 104 deploys machine-learned (ML) models 116-1 through 116-2 (collectively "ML models 116") for execution at the group of user devices 102. Prior to deployment, each of the ML models 116 is trained by a training module 112. The training module 112 programs each of the ML models 116 to make inferences based on signals received by a user device about whether or not a user of the user device has a condition. The ML models 116 may include any suitable model that is capable of making inferences based on signals received by a user device. The ML models 116 may include classification models and/or regression models. Such models are trained at the remote system and then deployed to user devices for local execution. Local execution does not imply that the ML models themselves are executable; rather, the ML models may be input to executable code that makes inferences by applying signals received at the device to the ML models.

Deploying copies of the ML model for execution at the user devices can have either or both of the following technical effects. First, the privacy of users of the devices can be preserved by making inferences based on signals collected at the user device and then anonymizing the inferences prior to sending them to the remote system. In this manner, the signals collected at the user device are not sent directly to the remote system, thereby preserving sensitive information contained within those signals. Second, execution of the ML model at the user device can allow inferences to be based on signals that are not available to the remote system. For example, many disease hotspots have poor connectivity to the Internet and, therefore, a user may not perform any web browsing from which inferences can be made. However, the user device may have access to other signals (e.g., a user's GPS coordinates, health-related data from a wearable device, application usage data) that can be used to make inferences when the user is not connected to the Internet.

Rather than risk sharing sensitive information generated by the ML models 116 over network 110, the user devices 102 use anonymizers 118-1 and 118-2 (collectively "anonymizers 118") to generalize information about any inferences made by the ML models 116. Aggregated statistics 120-1 and 120-2 (collectively "statistics 120") represent generalized location data and aggregated statistics about the inferences made by the ML models 116.

For example, the anonymizer 118-1 directs the ML model 116-1 to perform several inferences across different locations and times. The ML model 116-1 reports whether a user likely does or does not have a condition or does not have a condition for several times and locations. The anonymizer 118-1 generalizes the information from the ML model 116-1, so the output to the remote system 104 merely defines a rate of positive or negative inferences made over a period of time. The anonymizer 118-1 can remove the location from the output so the remote system 104 can identify a particular subregion (e.g., neighborhood) but not a particular device or user location (e.g., street address, coordinate location). The anonymizers 118 output the aggregated statistics 120 to be collected by the map module 114 of the remote system 104.

The map module 114 compiles the aggregated statistics 120 and infers statistics for other unreported models and regions. The map module 114 builds a high-level incidence map that identifies hotspots and coldspots for a particular disease with fine granularity. The map module 114 automatically adapts the incidence maps 122 to indicate changes in hotspots and coldspots of infected persons without providing any way for someone to derive user or user device identities. For example, the map module 114 can output the map 122-1 showing incidences of malaria in Brazil and the map 122-2 showing rate of infection of malaria or other arboviruses in a neighboring country or different part of Brazil. While able to show a rate of incidence at a high-level, the incidence map is finely detailed being based on aggregated statistics of inferences made from recent data captured at a user-device level, such as a neighborhood or street view. And while detailed, the maps 122 exclude personally identifiable information about individual persons who may be affected or their location because the anonymizers 118 ensure that such information is stripped from the aggregated statistics 120.

The map module 114 may execute its own machine-learned or another type of model to determine incidence rates. For example, the map module 114 trains and models incidence rates for a condition for a subregion based on aggregated statistics 120 collected for a different subregion. In other words, the map module 114 models, based on the aggregated statistics 120, a second rate of incidence of the condition for a second subregion from the multiple subregions at which neither of the user devices 102 is located.

The training module 112 regularly updates the ML models 116 and sends updated copies to replace the ML models 116-1 and 1162. Server-side logs and device logs are each an example of online data for generating incidence maps. The incidence map is regularly updated as well, for example, as new aggregated statistics are obtained from the user devices 102. Hence, the incidence maps 122 are current even if some of the data used to produce the incidence maps initially is old.

The environment 100, therefore, enhances existing predictive modeling techniques using statistical evaluation by the map generator 104 combined with federated (on-device) learning performed by the individual ML models 106. The example environment 100 estimates incidence rate of a condition (e.g., disease) across time and geographical areas using on-device online data collected in a privacy-first way. The example environment 100 estimates incidence rate of a condition in a global fashion through aggregating statistics 120, rather than merely adding up inferences made locally. The subregion-level information is regularly updated as new inferences, and new aggregated statistics, are made by the ML models 106. The remote system 104 outputs the incidence maps 122 to application subscribers executing at the systems 106 and 108 to use the maps as tools to combat current epidemics.

Figure 2:
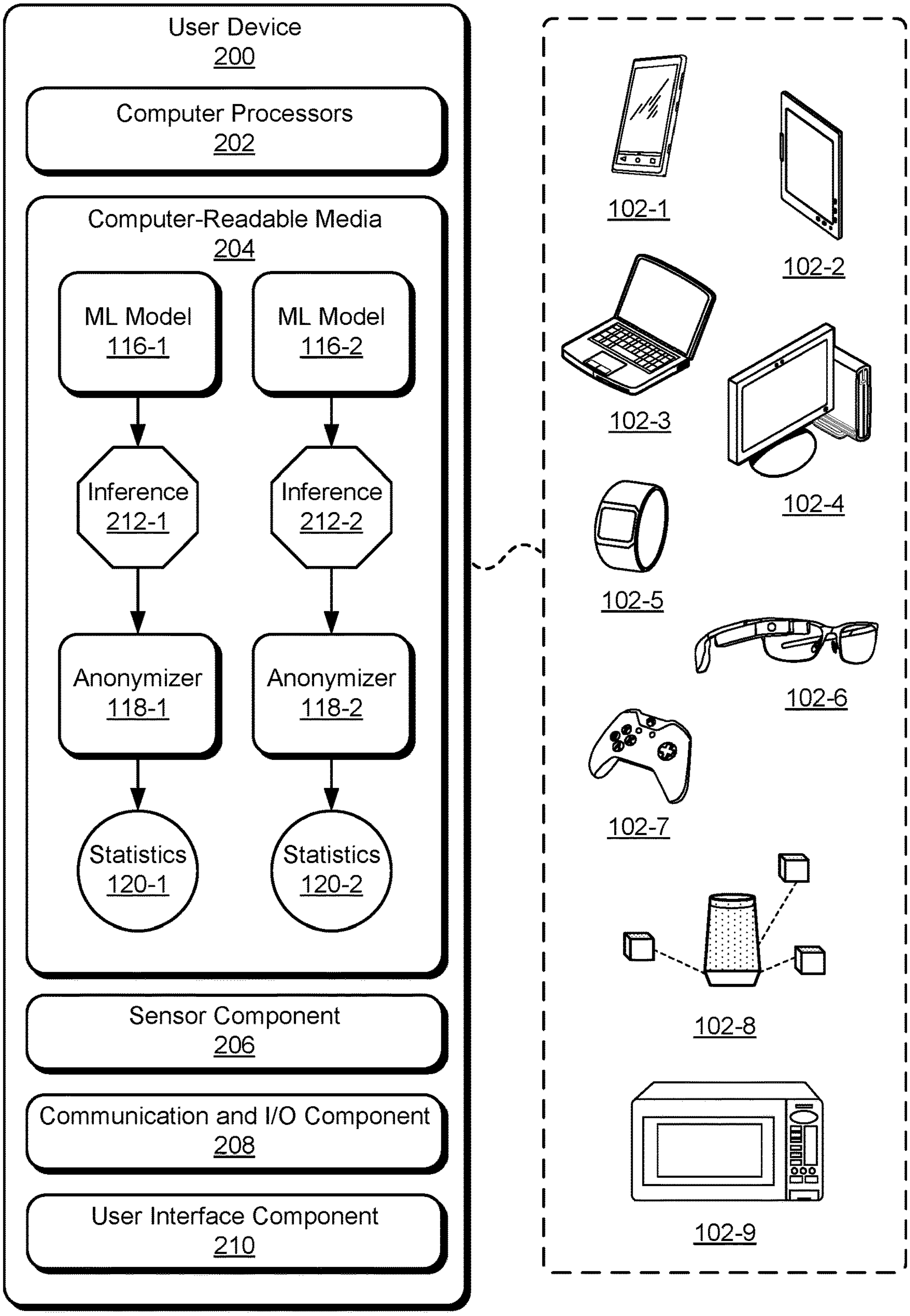
FIG. 2 illustrates an example of a user device that outputs aggregated statistics of inferences made by the user device for maintaining privacy during multi-modal on-device machine-learning.

FIG. 2 illustrates an example of a user device 200 that outputs aggregated statistics of inferences made by the user device for maintaining privacy during multi-modal on-device machine-learning. The user device 200 is an example of the user device 102 set forth in FIG. 1. FIG. 2 shows the user device 102 as being a variety of example devices, including a smartphone 102-1, a tablet 102-2, a laptop 102-3, a desktop computer 102-4, a computing watch 102-5, computing eyeglasses 102-6, a gaming system or controller 102-7, a smart speaker system 102-8, and an appliance 102-9. The user device 200 can also include other devices, such as televisions, entertainment systems, audio systems, automobiles, drones, trackpads, drawing pads, netbooks, e-readers, home security systems, doorbells, refrigerators, and other devices with multiple cameras and a face authentication system.

The user device 200 includes one or more computer processors 202 and one or more computer-readable media 204, and one or more sensor components 206. The user device 102 further includes one or more communication and input/output (I/O) components 208, and a user interface component 210, which can operate as an input device and/or an output device. The one or more computer-readable media 204 include the anonymizers 118, the ML models 116, which generate inferences 212-1 and 212-2 (collectively "inferences 212"), and the statistics 120.

The computer processors 202 and the computer-readable media 204, which includes memory media and storage media, are the main processing complex of the user device 102. The ML models 106, the anonymizers 118, and other applications (not shown) can be implemented as computer-readable instructions on the computer-readable media 204, which can be executed by the computer processors 202 to provide functionalities described herein.

The computer processors 202 may include any combination of one or more controllers, microcontrollers, processors, microprocessors, hardware processors, hardware processing units, digital-signal-processors, graphics processors, graphics processing units, and the like. The computer processors 202 may be an integrated processor and memory subsystem (e.g., implemented as a "system-on-chip"), which processes computer-executable instructions to control operations of the user device 102.

The computer-readable media 204 is configured as persistent and non-persistent storage of executable instructions (e.g., firmware, software, applications, modules, programs, functions) and data (e.g., user data, operational data, online data) to support execution of the executable instructions. Examples of the computer-readable media 204 include volatile memory and non-volatile memory, fixed and removable media devices, and any suitable memory device or electronic data storage that maintains executable instructions and supporting data. The computer-readable media 204 can include various implementations of random-access memory (RAM), read-only memory (ROM), flash memory, and other types of storage memory in various memory device configurations. The computer-readable media 204 excludes propagating signals. The computer-readable media 204 may be a solid-state drive (SSD) or a hard disk drive (HDD).

The sensor component 206 generally obtains contextual information indicative of operating conditions (virtual or physical) of the user device 102 or the user device 102's surroundings. The user device 102 monitors the operating conditions based in part on sensor data generated by the sensor component 206. Examples of the sensor component 206 include various types of cameras (e.g., optical, infrared), radar sensors, inertial measurement units, movement sensors, temperature sensors, position sensors, proximity sensors, light sensors, infrared sensors, moisture sensors, pressure sensors, and the like.

The communication and I/O component 208 provides connectivity to the user device 102 and other devices and peripherals. The communication and I/O component 208 includes data network interfaces that provide connection and/or communication links between the device and other data networks (e.g., the network 110), devices, or remote systems (e.g., servers). The communication and I/O component 208 couples the user device 102 to a variety of different types of components, peripherals, or accessory devices. Data input ports of the communication and I/O component 208 receives data, including image data, user inputs, communication data, audio data, video data, and the like. The communication and I/O component 208 enables wired or wireless communicating of device data between the user device 102 and other devices, computing systems, and networks, such as the remote system 104 and the network 110. Transceivers of the communication and I/O component 208 enables cellular phone communication and other types of network data communication.

The user interface device 214 acts as an input and output component for obtaining user input and providing a user interface, such as a graphical user interface including an incidence map generated from the aggregated statistics 120. As an output component, the user interface device 214 may be a display, a speaker or audio system, a haptic-feedback system, or another system for outputting information to a user. When configured as an input component, the user interface device 214 can include a touchscreen, a camera, a microphone, a physical button or switch, a radar input system, or another system for receiving input from the user. Other examples of the user interface device 214 include a mouse, a keyboard, a fingerprint sensor, an optical, an infrared, a pressure-sensitive, a presence-sensitive, or a radar-based gesture detection system. The user interface device 214 often includes a presence-sensitive input component operatively coupled to (or integrated within) a display.

When configured as a presence-sensitive screen, the user interface device 214 detects when a user provides two-dimensional or three-dimensional gestures at or near the locations of a presence-sensitive feature as the user interface is displayed. In response to the gestures, the user interface device 214 may output information to other components of the user device 102 to indicate relative locations (e.g., X, Y, Z coordinates) of the gestures, and to enable the other components to interpret the gestures. The user interface device 214 may output data based on the information generated by an output component or an input component, which, for example, the ML models 116 may use to make inferences 212.

The user device 200 generates the aggregated statistic 120 based on the inferences 212 made from signals obtained by the components 206 through 210. The user device 200 includes multiple ML models 116 to check for different conditions or as a redundancy check for the same condition. For example, the ML model 116-1 is trained to infer malaria based on online data (e.g., social media posts, messages) and other signals received by the user device 200. Similarly, the ML model 116-2 is trained to infer malaria or some completely different arbovirus based on the same, or different, online data and other signals received by the user device 200.

The ML models 116 are trained (e.g., using semi-supervised learning) based on noisy-labeled online data to make inferences about which signals, from the training data, are indicative of a particular condition. The ML models 116 perform federated learning, continuously executing locally on the user device 200 to, over time, accurately infer when a user of the user device 200 has the condition, when the user does not have the condition, or when the user having the condition is ambiguous.

The ML models 116 rely on the contextual information obtained by the sensors to more accurately determine the inferences 212. For example, a search for a medical term in a doctor's office might be a poor signal that the person searching has a disease connected to the medical term because there could be countless reasons to search for it in the doctor's office. However, the same search while at home or in bed during normal working hours for the user is a better signal the person searching has the disease.

The output from the ML models 116 is the inferences 212. The inferences 212 represent a single or multiple inferences made by the ML models 116 over one or more iterations (e.g., times and locations). In each inference-generating pipeline, the inferences 212 pass through one of the anonymizers 118 to remove any personally identifiable information from aggregated statistics 120 generated from the inferences 112. For example, rather than associate the statistics 120-1 with a location or location history of the user device 200 when the inferences 212-1 was made, the statistics 120-1 are associated with a subregion or a generalized location that encompasses the particular location or location history where the interference 212-1 was made.

To further ensure anonymity and prevent a model's inferences from being traced back to an individual, the anonymizers 118 introduce strategic noise to the statistics 120. For instance, by randomly introducing negative or positive statistics that have a zero mean, into the aggregated statistics 120, the remote system 104 can directly make inferences about the statistics collected as a whole but not about particular individuals. These, as well as secure aggregation or other techniques may be used to remove all personally identifiable information from the statistics 120 the remote system 104, or another device can build an incidence map from the data. With ongoing federated learning occurring on individual devices like the user device 200, more timely, accurate, and unskewed data can be used to validate whether or not a user has a disease, which leads to accurate risk maps, thereby enhancing the impact of vaccination strategies and efficacy of interventions in affected areas.

Figure 3:
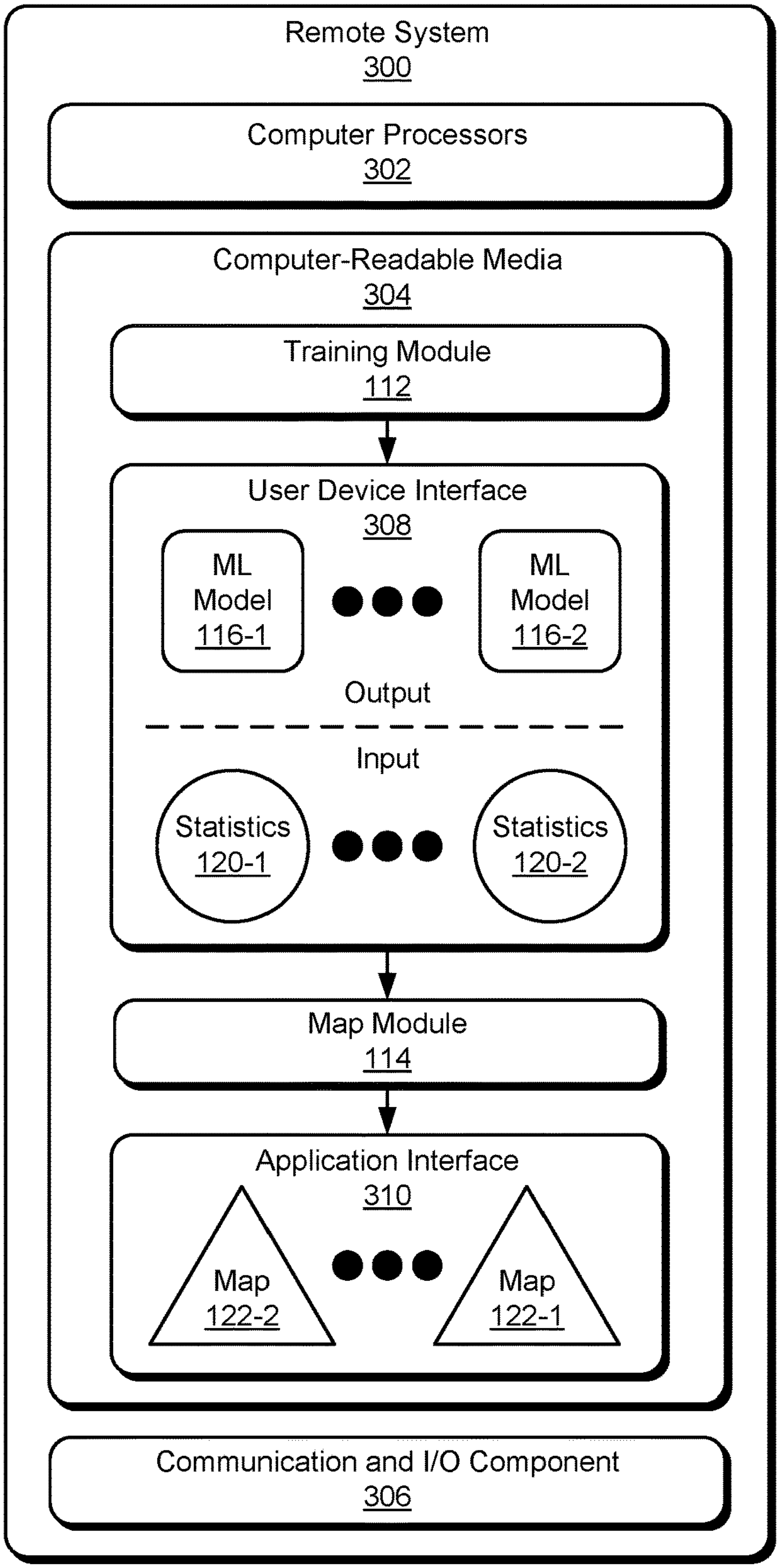
FIG. 3 illustrates an example of a remote system that generates incidence maps based on aggregated statistics output from a group of user devices for maintaining privacy during multi-modal on-device machine-learning.

FIG. 3 illustrates an example of a remote system 300 that generates incidence maps based on aggregated statistics output from a group of user devices for maintaining privacy during multi-modal on-device machine-learning. The remote system 300 is an example of the remote system 104 set forth in FIG. 1. The remote system may be any variety of example devices, including consumer devices as well as servers, blades, mainframes, or any other computing system.

The remote system 300 architecture is similar to the user device 200, including computer processors 302, computer-readable media 304, and communication and I/O devices 306. However, unlike the computer-readable media 204, the computer-readable media 304 includes the training module 112, the map module 114, a user device interface 308, and an application interface 310.

The user device interface 308 outputs information that directs federated machine-learning performed by the user devices 102 and collects information generated in response. The user device interface 308 enables the remote system 300 to output copies of the ML models 316 to the user devices 102. The user device interface 308 also enables input of the aggregated statistics 120 from the user devices 102. The user device interface 308 acts with the communication and I/O component 208 to transmit and receive data over the network 110, for example.

The application interface 310 outputs incidence maps 122 to application subscribers executing at other remote systems or devices. For example, the containment system 106 executes a real-time containment application to deploy barriers or roadblocks to prevent the spread of a condition. The real-time containment application gets its real-time update of the incidence maps 122 from the application interface 310. As another example, the treatment system 108 executes a treatment application that shows progress of treatments and current outbreak conditions in seemingly real-time. Current conditions, as well as the efficacy of treatment can be recognized in minutes, as opposed to days, months, or years.

The training module 112 initially trains each of the ML models 116. The training module 112 may initially train based on online data (e.g., online user interactions "clicks"), but may also train the ML models 116 based on other signals, such as a daily routine (e.g., location history, application interactions) and a calendar (e.g., including online calendars, message services). The training module 112 collects the training data from an external source, such as a search service, financial service, or another source of genericized, online data.

The training module 112 processes online data to read various corpora already within the online data (e.g., query datatype, click datatype) and outputs a custom corpus that contains the signals needed for predicting and pinpointing conditions (e.g., query, location, routine, noisy label). The training module 112 can infer additional data beyond online data such as clicks. A user of the device 200 viewing a webpage presented at user interface component 214 (e.g., clicking) about influenza treatment is a noisy label for training the ML models 116. However, viewing content about influenza with added contextual information from the sensor components 206 about the user staying at home while normally they would be expected at work noisily suggests they may have influenza (at least with a higher probability than a device that does not receive the same signals). The training module 112 can derive a noisy label for online data and join the noisy label with other signals to improve predictions. For example, entities (e.g., uniform resource locators) navigated in response to clicks may or may not be used by the training module 112 as additional data to program the ML models 116 to infer conditions of a user.

The training module 112 trains the ML models 116 to generate one of three inferences: clear-positive for a condition, ambiguous, and a clear-negative for the condition. Some signals (e.g., queries), when present, are clear positive signals that strongly indicate a user has a disease. For example, searches for influenza treatments are strong positive signals of the disease.

Each signal gives a different and somewhat complementary view of the health state of the user. Combining noisy labels produces a better estimate of health state than a signal alone. Some signals lead to ambiguous inferences indicating that the disease is one of several possible conditions. For example, searches for influenza vaccines lead to ambiguous inferences because reading about a vaccine does not directly indicate an acute influenza infection. The training module 112 directs the ML models 116 to make strong positive, negative, and ambiguous inferences. Ultimately, each of the ML models 116 outputs an indication of whether a person associated with a user device has a condition (e.g., a disease) at a particular time.

When a signal can lead to two different diseases or conditions, topicality scoring, or other techniques can be used to avoid false positive or false negative labels of training data. For example, "flu symptom" pages may be labeled as aiding in inferring the flu, but "flu vaccine" pages may not be. The topicality score of a page that more closely matches the topicality score of a "flu vaccine" page instead of a "flu symptoms" page is a signal the document is mainly about "flu vaccines" instead of "flu symptoms".

Orthogonal signals enable noisy labeled queries. Examples of such signals include a location history or a daily routine. Location history or daily routine can be generated from collecting sensor data by the sensor component 206. A person might have one of many conditions if the person stays at home while searching for information about the flu. If the routine of the person indicates that they are normally elsewhere, then the person is even more likely to have one of the conditions. Using such a process, the training module 112 trains the ML models 116 to infer a person's condition.

As an example of how the training module 112 trains the ML model 116-1, consider, as a first iteration, the training module 112 treats a signal (e.g., a query) to be positive for a condition ("is sick") when the signal is received in a particular location. Not that the query or signal was associated with a particular location through indexing, but that the signal originated or was received at the particular location. During subsequent iterations, available queries in a given subregion surrounding the location, and locations of other inferences are assigned noisy labels indicating a condition or not. The ML model 116-1 is trained by the training module 112 on the noisy-labeled data. The ML model 116-1 runs in inference mode on a withheld set of training data (e.g., queries), and the ML model 116-1 is tweaked until inferences from the ML model 116-1 are comparable to "golden" or expected labels.

When being trained, the ML model 116-1 generates additional training data amenable for self-supervised and semi-supervised learning. Each query or "signal" represents a high-dimensional space of features extracted from the signal's broad context. These signals can be reused by the ML model 116-1 to improve inferences made from future signals. As an example, the "broad context" includes documents clicked upon displaying a query's search results, attributes of those documents (e.g., are they about flu), attributes of the click itself (e.g., how long did the user spend reading the page), state of the user irrespective of, or dependent on, what happens in a search (e.g., is the user active physically are they following their expected routine, is their phone charging at home when they are normally at work or a gym).

The training module 112 can cause the ML models 116 to estimate the probability of each example x having a positive label, Pr(y=positive|x), a variety of active learning approaches can be used to optimize a data labeling budget. Specifically, entropy-based uncertainty sampling to label a small set of examples that maximize entropy reduction, where at each turn the most "valuable" example to label is given by (Equation 1):

$$x' = \operatorname{argmax}_x \sum_i -Pr(y=i \mid x)\log P(y=i \mid x) \quad \text{Equation 1}$$

The models 116 can be further improved by bootstrapping over positives. After the ML models 116 label data in inference mode, queries labeled by the ML models 116 that are positive but probably incorrect are then fed back to re-train the models 116 with a negative label, so similar mistakes are less likely to happen in the next round. Similarly, bootstrapping can be done on location-derived labels or a joint of the two labels.

The map module 114 collects statistics 120 aggregated by the devices 102 and outputs incidence maps 122 via application interface 310. The map module 114 makes statistical inferences using the aggregated output of the ML models 116.

Evidence fusion is performed over the current probability by blending global incidence with the local estimate. Assuming independence, which generally not true, but makes the problem traceable. Aggregation helps with reducing the effects of this assumption. A joint estimate of Pr[D is sick at t|local data, global data] is calculated. For brevity, let S denote the event that D is sick at time t, L local data, and G global data. For example, Equation 2 is Pr [S|L, G], which equals:

$$\frac{Pr[S \mid L]Pr[S \mid G]}{[Pr[S/L]Pr[S/G] + (1 - Pr[S/L])(1 - Pr[S/G])} \quad \text{Equation 2}$$

Equation 2 expresses the fraction of probability mass where both sources of evidence agree D is sick at time t over the total probability mass that they agree. More-complex fusion models are possible, including weighting by the confidence of each piece of evidence, and adding sequential evidence (e.g., Equation 2 ignores Pr[D is sick at time t−1]), assuming distributions over values, beta transform, etc.

Since incubation is two time-units, also needing consideration is a scenario where the user became infected at B at time 2 and only indicated signals of illness at time 3 (while already visiting a different location). At this point, D can locally optimize against these updated probabilities (assuming for a moment they are ground truth, following the expectation-maximization approach, and pulling appropriate local logs data with the appropriate time lag). The remote system 104 can update training module 112 to share regular updates to the other ML models 116, securely sharing gradient updates with other devices 102 to improve the personal-level models 116. Aggregate predictions from this shared model 116-1 are continuously checked on the remote system 104 against (historical and live) validation data, and if a new model exceeds the quality of previous models, the remote system 104 deploys the new versions of the models 116. Temporarily, devices continue running inference with previous versions of the model 116 in parallel with the new version of the model 116 until the new version is verified.

Validation data can come in several forms: independent population-level estimates (e.g., center for disease control estimates, when available), user survey data (e.g., Jackson's symptom checker), and aggregate lab result data. The process above is repeatable to constantly train the ML models 116 with new updated values for every device D, and eventually converges to a local optimum.

For many conditions, user-level probabilities (estimates of the rate of infections) are not needed. For example, to spray against mosquitoes or deploy vaccination against influenza, the remote system 104 only needs to train models 116 to identify which geographical areas should be prioritized with treatment, as opposed to trying to identify the most infected locations. In these situations, the problem can be simplified using end-to-end gradient optimization by taking a collection of signals in a given geo-time cell and learn a unified mapping from it to the incidence rate. The advantage of this approach is that individual-level decisions are completely implicit and signals are directly optimized against population-level ground truth estimates. This eliminates several sources of noise in the system.

Figure 4:
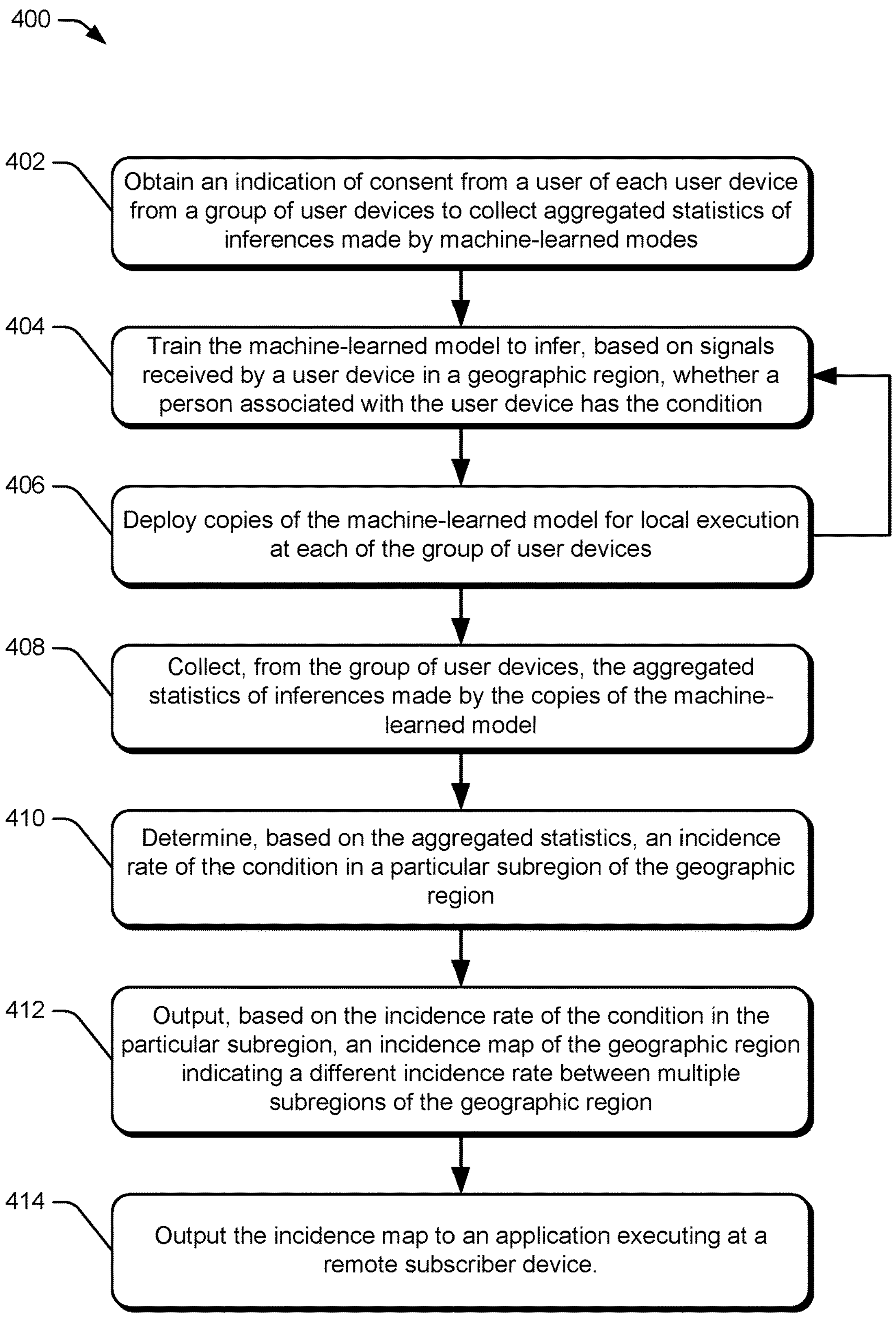
FIG. 4 illustrates an example method performed by a user device for maintaining privacy during multi-modal on-device machine-learning.

FIG. 4 illustrates an example method performed by a remote system for maintaining privacy during multi-modal on-device machine-learning. The method 400 can include additional or fewer steps than those shown in FIG. 4 and may be performed in a different order. The method 400 is described below in the context of the remote system 104.

At 402, the remote system 104 obtains an indication of consent from a user of each user device from a group of user devices to collect aggregated statistics of inferences made by machine-learned models. For example, the user devices 102 require users to provide input confirming that the remote system 104 has permission to collect statistics of inferences made by local signals, under the condition that the statistics and other information about the user are protected, treated, anonymized, or otherwise not traceable back to the user or the user devices 102.

At 404, the remote system 104 trains a machine-learned model 116 to infer, based on signals received by user devices 102 in a geographic region, whether a person associated with the user devices 102 has the condition. For example, the training module 112 uses ground truth data and other data sources to train ML models 116 to make inferences about different conditions. The remote system 104 can run the ML model 116 in inference mode based on ground truth data for the geographic region and the signals received by a test user device in the geographic region, to initially train the ML model 116, before deploying the ML model 116 to the user devices 102.

The remote system 104 may repeat step 404 and retrain the ML model 116 based on updated data or emulated data. The training module 112 may emulate training data including examples of the signals received by the user devices 102 when the persons associated with the user devices 102 had or has the condition and examples of the signals received by the user devices 102 when the persons associated with the user devices 102 does not or did not have the condition. The training module 112 may further analyze the aggregated statistics alongside other data to update further and train the ML models 116. At 404, the remote system 104 may retrain the ML model 116 based on the emulated training data and generate new copies of the ML model 114 for redeployment to the user devices 102.

At 406, the remote system deploys copies or new copies of the ML model 116 for local execution at each of the group of user devices 102. For example, the remote system 104 sends the ML model 116 via the network 110 to each of the user devices 102.

At 408, the remote system 104 collects, from the group of user devices, aggregated statistics of inferences made by the copies of the machine-learned model. For example, the map module 114 receives a first portion of the aggregated statistics 120-1 from the user device 102-1. From the first portion of the aggregated statistics 120-1, the map module 114 infers a first subregion from multiple subregions of a geographic region. The map module 114 generalizes a location associated with the aggregated statistics 120-1 to a unit of area or subregion that surrounds the location, so any inference made from the statistics 120-1 is not traceable back to the user.

At 410, the remote system 104 determines, based on the aggregated statistics, an incidence rate of the condition in a particular subregion of the geographic region. The map module 114 attributes, based at least in part on the aggregated statistics 120-1, a first rate of incidence of the condition to the first subregion and generates the incidence maps 122 of the geographic region by indicating the first rate of incidence of the condition throughout the first subregion. Next, the map module 114 receives a second portion of the aggregated statistics 120-2 from a second user device 102-2 and repeats the above process at 408, but for the second subregion to generate a second rate of incidence for a second subregion.

In some cases, inferences are made when the user devices 102 are at different locations than where users of the devices 102 reside or perform their normal routine. As such, the aggregated statistics 120 collected from the user devices 102 in one subregion may be more useful for determining an occurrence of a condition in a different subregion other than the subregion from which the statistics 120 are collected. The map module 114 may, therefore, attribute a rate of incidence to a second subregion based on aggregated statistics collected from a first subregion. The rate of incidence for the second subregion may be similar to the rate of incidence for the first subregion. The rate of incidence for the second subregion may be completely different, however, for instance, if the rate of incidence for the second subregion is based on the rate of incidence for the first subregion in addition to rates of incidence for other subregions.

At 412, the remote system 104 outputs, based on the incidence rate of the condition in the particular subregion, an incidence map of the geographic region indicating a different incidence rate between multiple subregions of the geographic region. For example, the map module 114 outputs the maps 122-1 and 122-2.

At 414, the remote system 104 outputs the incidence map to an application executing at a remote subscriber device. For example, the incidence maps 122 are transmitted to the containment system 106 and the treatment system 108 from each of which local applications use the incidence maps to perform containment or treatment operations.

Figure 5:
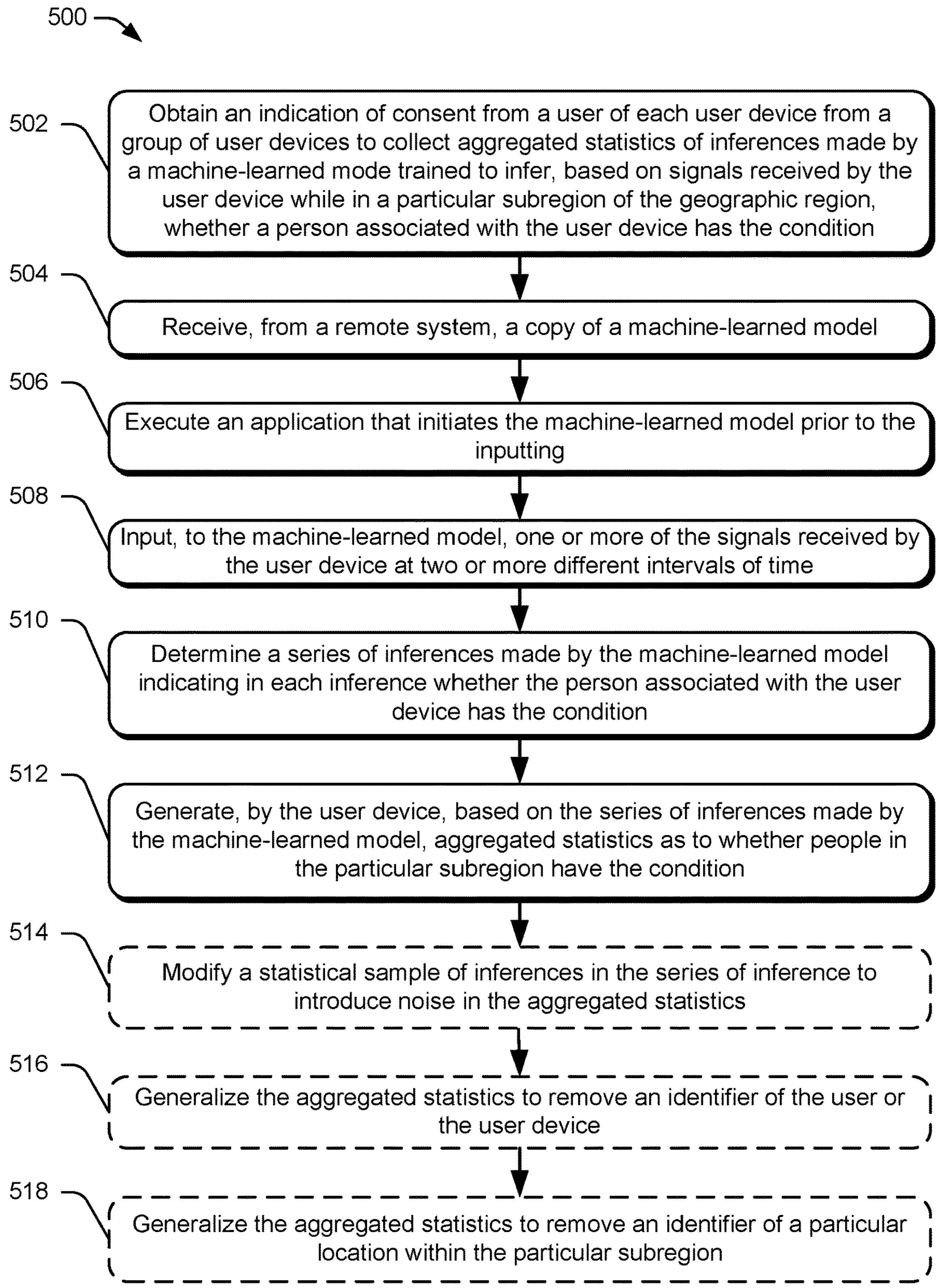
FIG. 5 illustrates an example method performed by a remote system for maintaining privacy during multi-modal on-device machine-learning.

FIG. 5 illustrates an example method performed by a user device for maintaining privacy during multi-modal on-device machine-learning. The method 500 can include additional or fewer steps than those shown in FIG. 5 and may be performed in a different order. The method 500 is described below in the context of the user device 200.

At 502, the user device 200 obtains an indication of consent from a user of each user device from a group of user devices to collect aggregated statistics of inferences made by a machine-learned model trained to infer, based on signals received by the user device while in a particular subregion of the geographic region, whether a person associated with the user device has the condition. In other words, the user device 200 receives user input from a user consenting to the collecting of statistics of inferences made from local execution of a machine-learned model.

At 504, the user device 200 receives, from a remote system, a copy of a machine-learned model trained to infer, based on signals received by the user device while in a particular subregion of the geographic region, whether a person associated with the user device has the condition. For example, the user device 200 receives a copy (ML model 116-1) of the ML model 116 via the network 110 and from the remote system 104.

At 506, the user device 200 executes an application that initiates the machine-learned model. For example, the ML model 116-1 can execute as part of an operating platform (OS) of the user device 200 or as part of an application, such as a travel application, an assistant application, a health application, or another software component accessible from the user device 200.

At 508, the user device 200 inputs, to the ML model 116-1, one or more of the signals received by the user device 200 at two or more different intervals of time. For example, the signals are search queries, calendar events, or other contextual information, e.g., obtained from the sensor components 206. The signals may be examples of online data sent or received by the user device 200.

At 510, the user device 200 determines a series of inferences made by the machine-learned model indicating in each inference whether the person associated with the user device 200 has the condition. For example, the ML model 116-1 can execute and generate inferences that overtime forms a series of inferences 212-1 from which the anonymizer 118-1 produces aggregated statistics 120-1 as to whether people in the particular subregion have the condition. At 512, the user device 200 generates, based on the series of inferences 212-1 made by the machine-learned model 116-1, aggregated statistics 120-1 as to whether people in the particular subregion have the condition.

The user device 200 performs one or more of the optional steps 514, 516, or 518. At 514, the user device 200 modifies the aggregated statistics 120-1 by introducing noise, for example, by modifying a statistical sample of the inferences in the series of inference 212-1 to introduce noise in the aggregated statistics 120-1. The aggregated statistics 120-1 can include random noise with a zero mean so while the statistics 120-1 may not be representative of the user, they are representative of a generic user for purposes of attributing a condition. At 516, the user device 200 modifies the aggregated statistics 120-1 by generalizing the aggregated statistics to remove an identifier of the user or the user device 200. At 518, the user device 200 modifies the aggregated statistics 120-1 by generalizing the aggregated statistics to remove an identifier of a particular location within the particular subregion prior to outputting the indication of the aggregated statistics to the remote system. Modifying the aggregated statistics 120-1 in either of these ways helps further promote privacy of the user.

Figure 6:
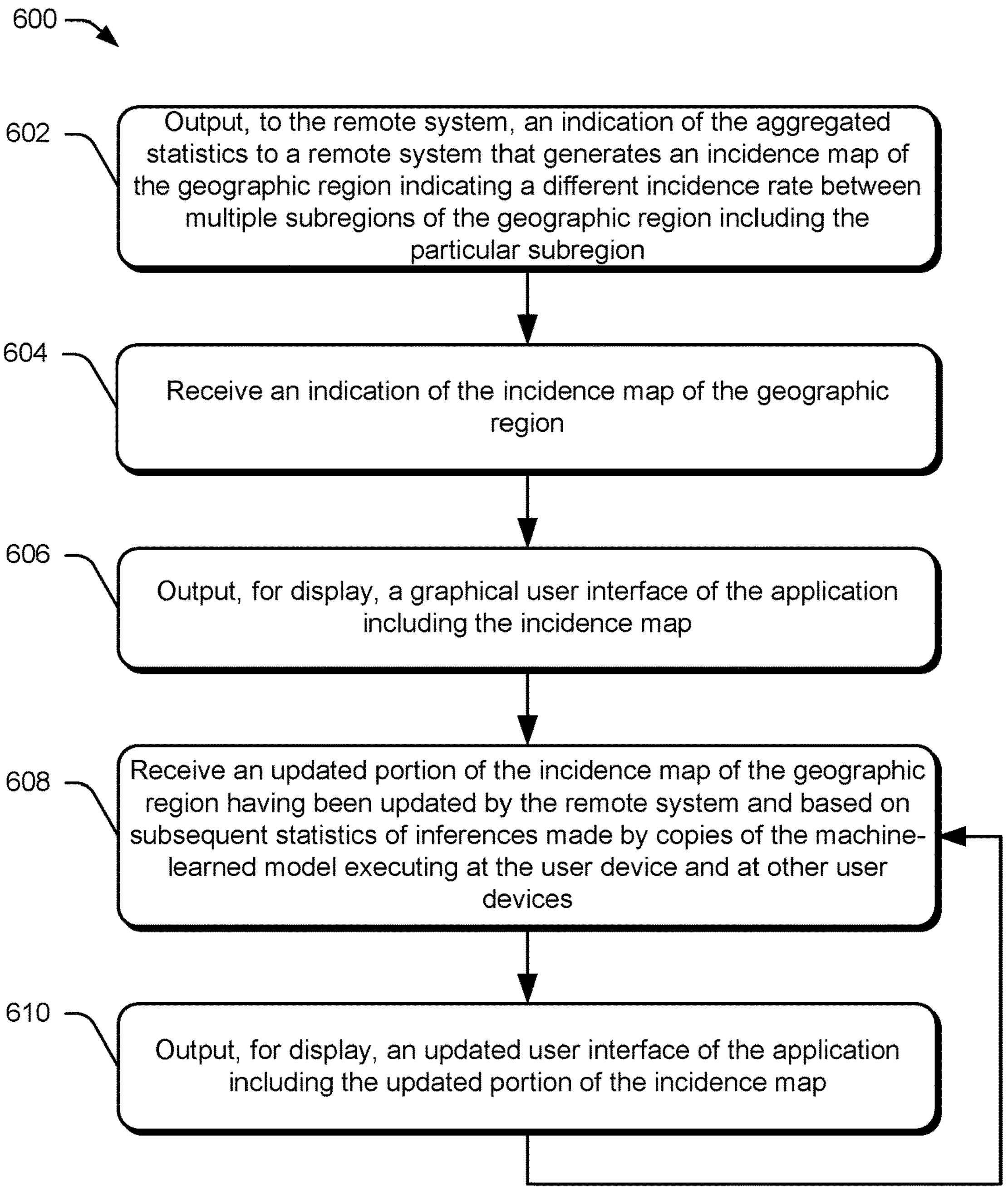
FIG. 6 illustrates an example method performed by a computing system for maintaining privacy during multi-modal on-device machine-learning.

FIG. 6 illustrates an additional example method performed by a user device for maintaining privacy during multi-modal on-device machine-learning. The method 600 can include additional or fewer steps than those shown in FIG. 6 and may be performed in a different order. The method 600 is described below in the context of the user device 200.

At 602, the user device 200 outputs an indication of the aggregated statistics to the remote system 104. This enables the remote system 104 to generate incidence maps 122-1 and 122-2.

At 604, the user device 200 receives an indication of the incidence map 122-1 of the geographic region. For example, the user device 200 may be an application subscriber of the remote system 104, not just a data source. This means the user device 200 may receive the incidence map 122-1 in addition to providing statistics used to produce the map 122-1.

At 606, the user device 200 outputs, for display, a graphical user interface, including the incidence map 122-1. For example, the user device 200 may present the incidence map 122-1 on the user interface component 210.

At 608, the user device receives an updated portion of the incidence map, having been updated by the remote system 104. The updated portion is based on subsequent statistics of inferences, as to whether people in particular subregions have the condition, made by copies of the machine-learned model 116 executing at other user devices 102. For example, the user device 200 and other user devices output subsequent (aggregated) statistics made from subsequent inferences by the ML model 116-1 and other ML models. Like the original statistics, the subsequent statistics indicate whether people in the particular subregion have the condition.

At 610, responsive to outputting the subsequent statistics, the user device 200 receives an updated portion of the incidence map 122-1 and outputs, for display, an updated user interface the updated portion of the incidence map. This way, the user device 200 can receive updated portions of the incidence map 122-1 rather than an entire map.

Figures 1, 7:
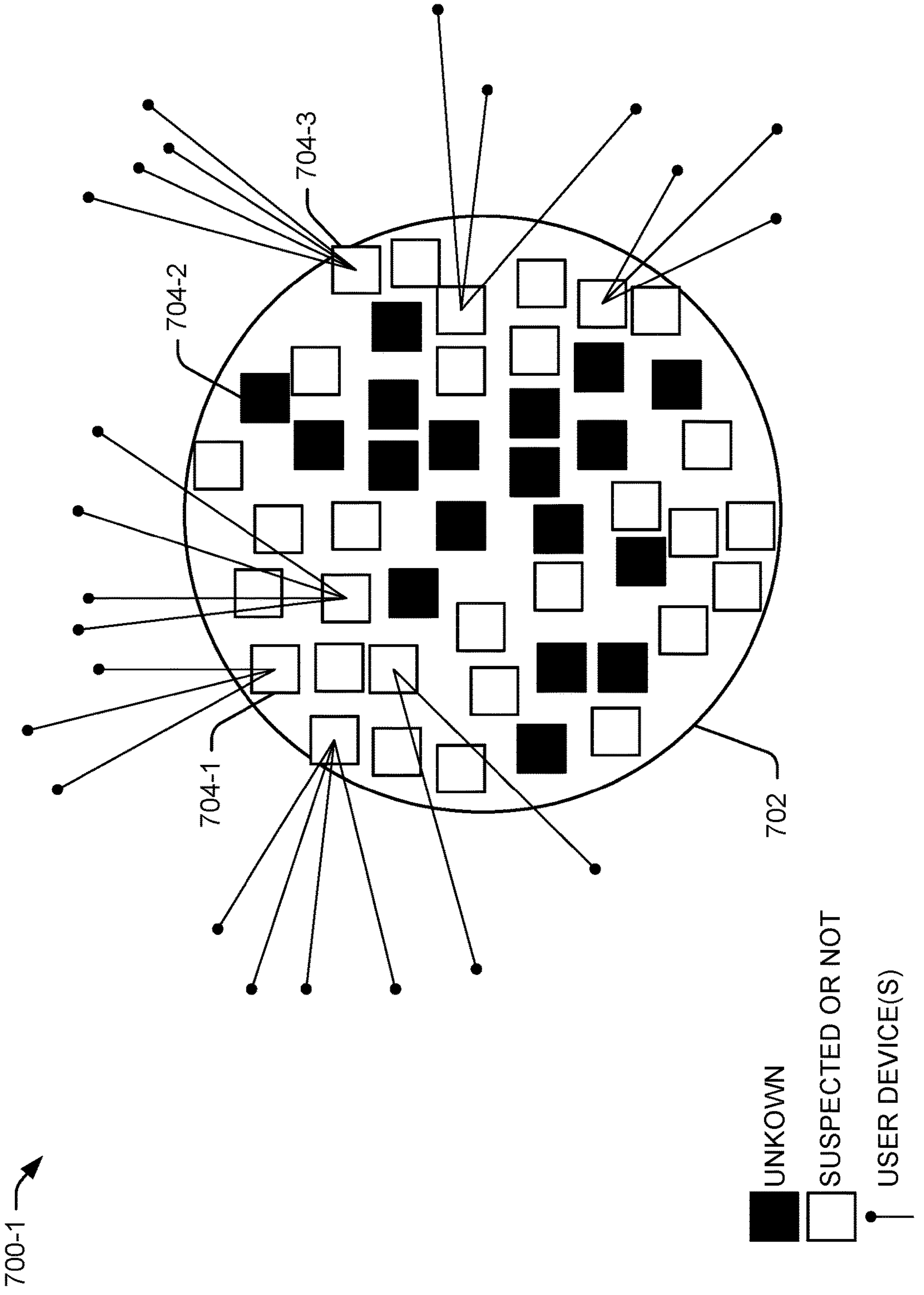
Figures 2, 7:
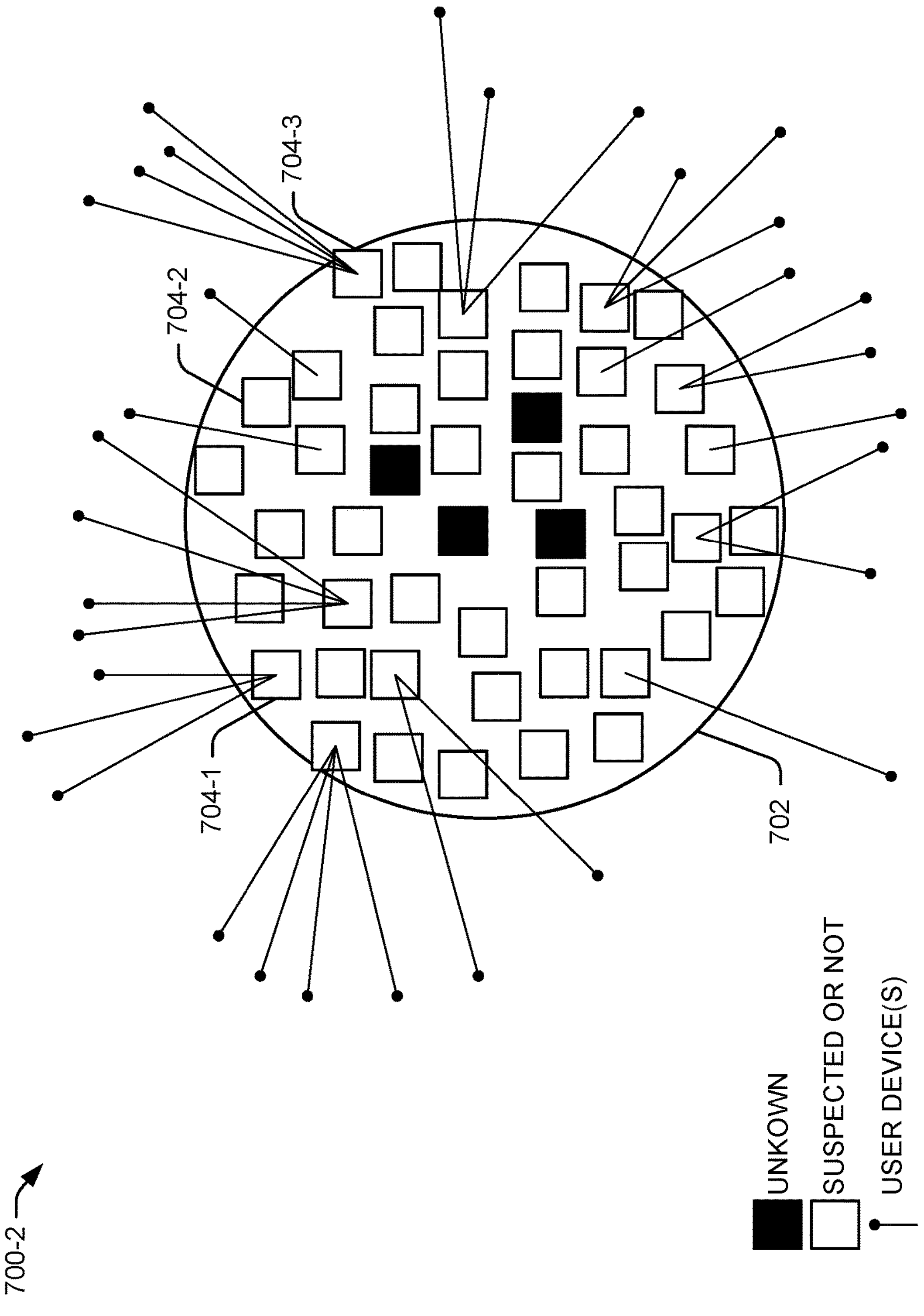
Figures 3, 7:
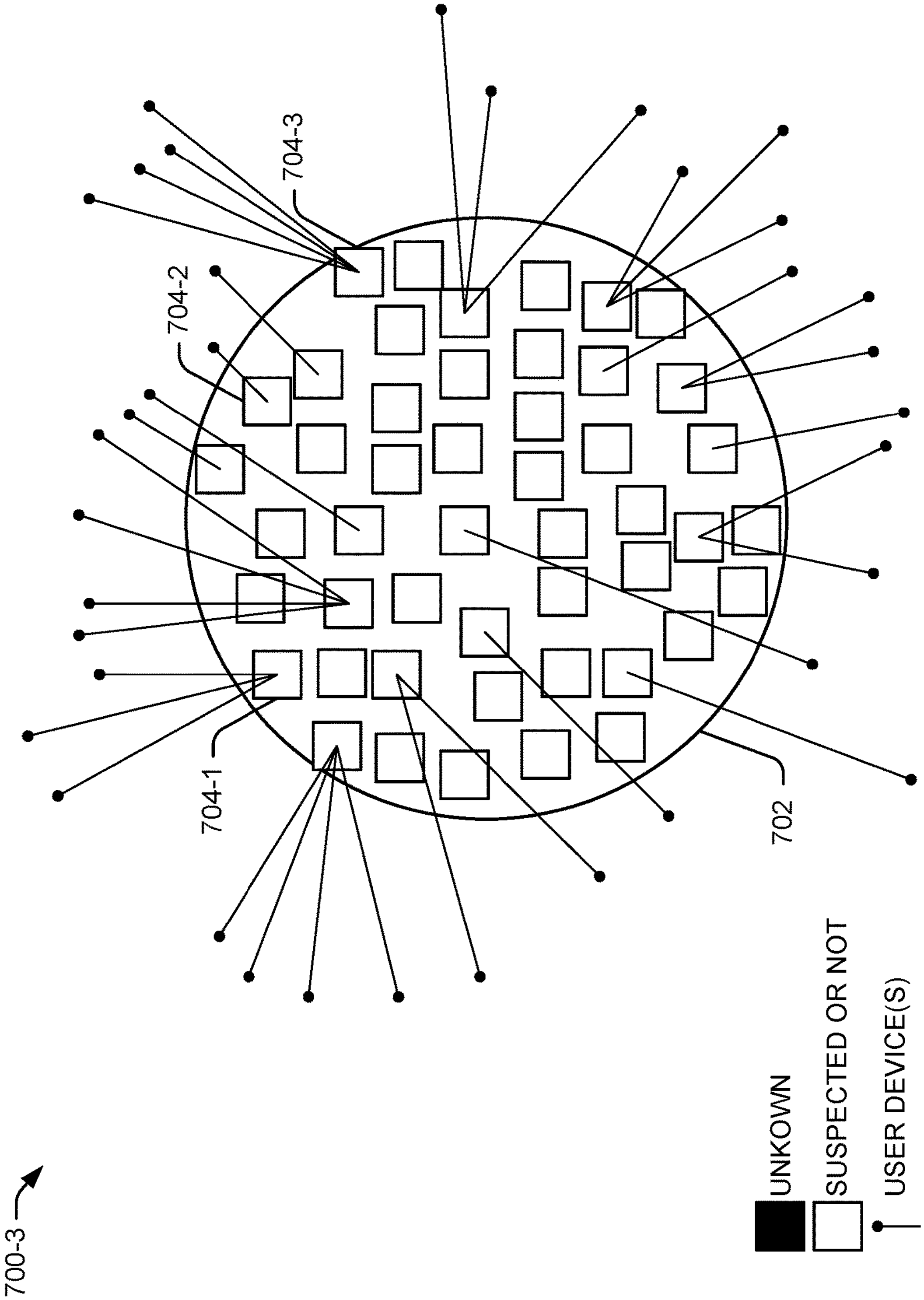

FIGS. 7-1 through 7-3 illustrate an example progression of an incidence map 700-1 through 700-3 as a computing system collects aggregated statistics, over time. The incidence maps 700-1 through 700-3 are examples of the incidence maps 122 generated as the map module 114 collects aggregated statistics 120 from multiple user devices 102 within a geographic region 702. In FIGS. 7-1 through 7-3, the user devices 102 are illustrated as pins (capped line segments) within different subregion units (black and white squares), including subregions 704-1 through 704-3, within the geographic region 702. The white subregion units indicate subregions recognized by the map module 114 as having or not having a particular condition. The black subregion units indicate ambiguous subregions where the map module 114 is undecided.

Consider a hypothetical influenza outbreak in Australia. Traditionally, user devices 102 in the geographic region 702 of Australia, may upload data into a cloud computing environment where the data is processed for various application purposes. This data is often personal, sensitive, and in principle, almost always linkable to the individuals or at least the user device 102. An alternative to personal data is publicly available ground truth data, e.g., incidence rate of influenza-like illness for postal codes over weeks provided by Australian government agencies. While not personal, the ground truth data is often too granular or out-of-date and not useful in generating an incidence map that would be sufficient for containment or treatment.

To generate an accurate incidence map for influenza in the geographic region 702, the remote system 104 blends the two different types of datasets (aggregated statistics collected from the devices 102 and ground truth data) in the map module 114. The map module 114 blends the data and makes statistical maps 700-1 through 700-3 about individual subregions within the geographic region 702.

The progression from the incidence maps 700-1 through 700-3 shows how, with more aggregated statistics 120, from more user devices 102, the map module 114 can generate a complete incidence map. The map module 114 can fill in the black subregions and generate a complete incidence map 700-3.

The remote system 104 relies on the training module 112 to get the ML models 116 started with aggregating and reporting statistics. The ML models 116 enable the map module 114 to leverage on-device accuracy from local inferences made from locally received signals. The map module 114 collects the statistics to produce accurate incidence maps 700-1 through 700-3, still with complete anonymity.

The accuracy and anonymity of each of the incidence maps 700-1 through 700-3 increases as more statistics are collected from more devices 102, in more subregions. Individually, the statistics are noisy and ambiguous for health modeling purposes. For example, even if a user in Australia searches with the user device 102-1, with a specific query like “fever” or “sore throat” when the user device 102-1 is in a subregion 704A (e.g., Sydney), this search signal can mean many things besides the user having the flu, even if searched many times in many different contexts. The search could be for obtaining cold symptoms on behalf of a loved one outside Australia, for obtaining information for a paper or article about the flu, or many other reasons. However, aggregated statistics 120 from multiple user devices 102 in multiple subregions 704-1 and 704-3 can be useful for health modeling purposes in those and other subregions, such as subregion 704-2 from where no data is collected. The map module 114 sidesteps the need for obtaining data with explicit health labels at an individual device-level, which has been found to be problematic to achieve at scale while preserving privacy.

Advancing the Australia example, where the user of the user device 102-1 searches for [fever and sore throat], the user may have searched while recently in the subregion 704-3. Subregion 704-3 has confirmed influenza outbreaks, and patterns of the user’s online or offline behavior (e.g., staying home from work) now that the user has returned to subregion 704-1 are similar to those in subregion 704-3 who eventually searched for more specific signs of flu. The map module 114 can adjust the map 700-1 to indicate that the influenza is more likely around the subregion 704-3 where the user device 102-1 collected the signals but also around the subregion 704-1 where the user device 102-1 reported the signals. The map module 114 updates the map 700-1, all while the private data of the user remains localized to the user device 102-1, sparse, and ambiguous. The incidence maps 700-2 and 700-3 show the entire geographic region 702 with a suspected probability or rate of incidence plotted, eventually, for each subregion.

Aggregated statistics collected from devices 102 in subregions 704-1 and 704-3, can be used to map influenza in a subregion 704-2 where no pins exist. The incidence map 700-2, for example, shows the subregion 704-2 classified as having a condition or not, even though no local data has been collected from the subregion 704-2. Raw data remains private and is not shared off of the devices 102. Instead, the map module 114 relies on statistical patterns in the aggregated statistics collected from the multiple devices 102 in subregions 704-1 and 704-3, to infer what's happening in subregion 704-2.

Highlighting subregions where a condition is occurring, not occurring, or unknown enable application subscribers that receive the maps 700-1 through 700-3 to identify geographical boundaries to set up containment and treatment operations to fight the disease. Because signals are aggregated over a large number of devices 102 (lots of pins shown in the maps 700-1 through 700-3), the techniques and systems enable incidence maps with fine detail, but with a more-global view into the world.

Figures 1, 8:
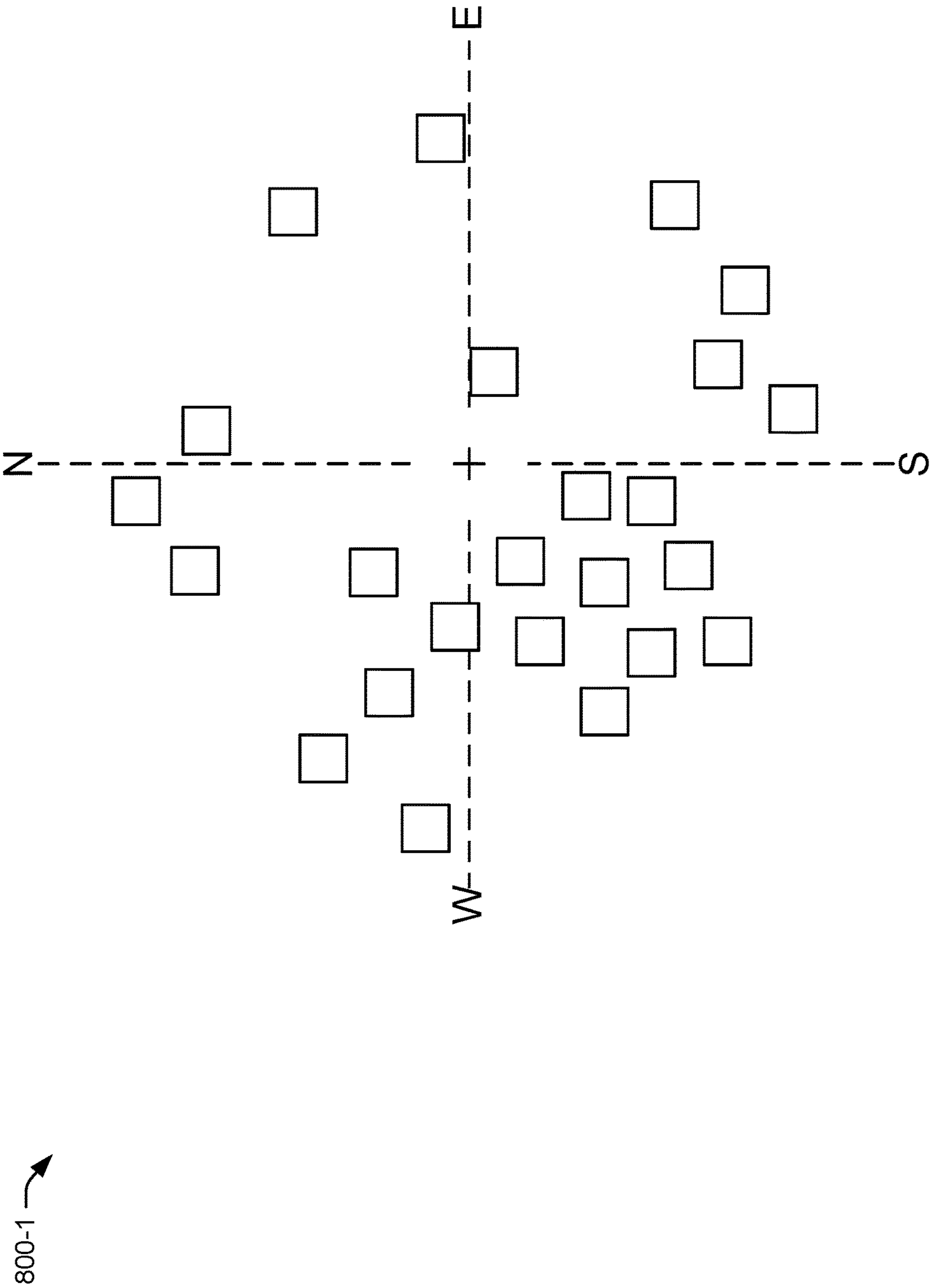
Figures 2, 8:
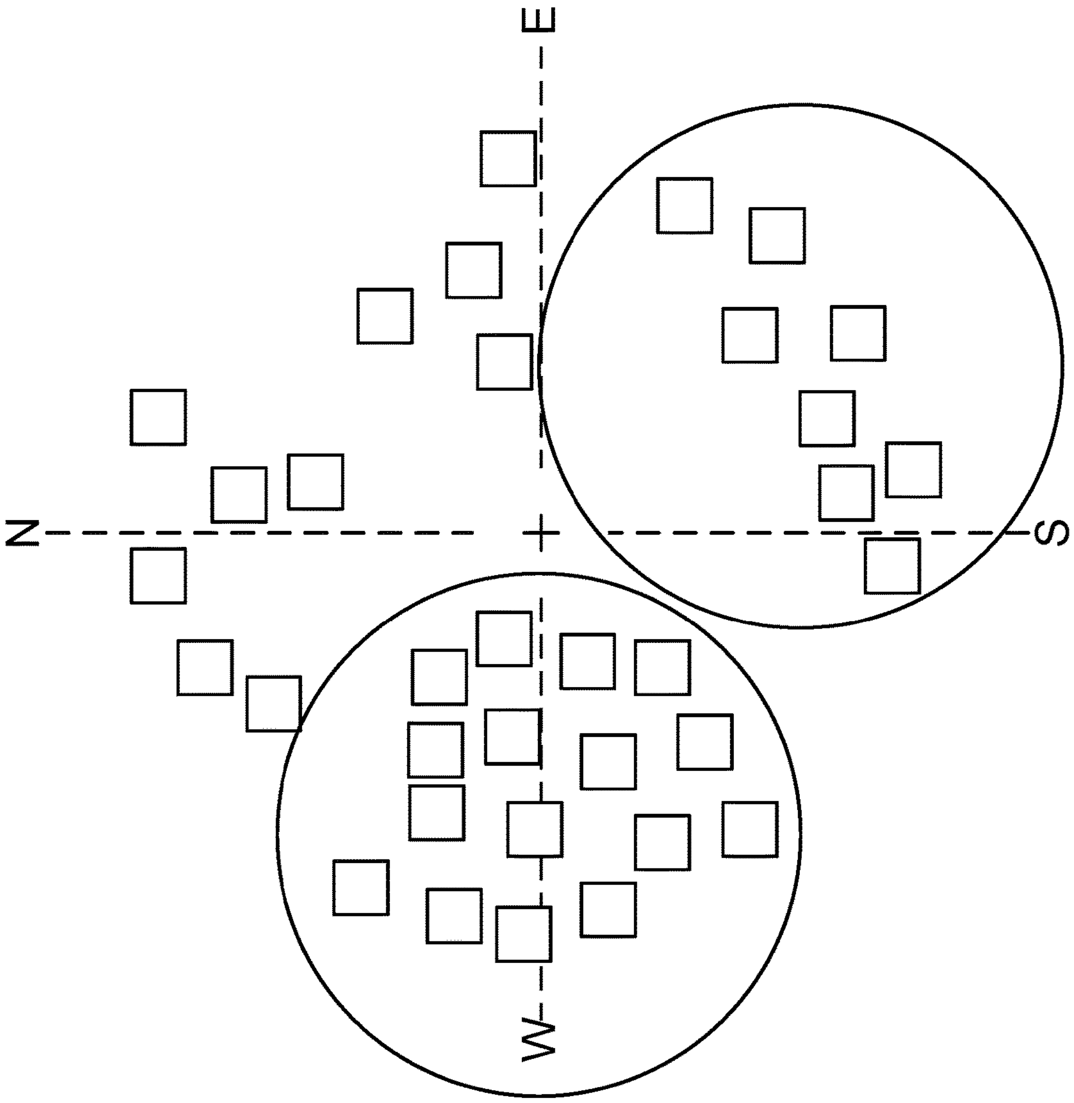
Figures 3, 8:
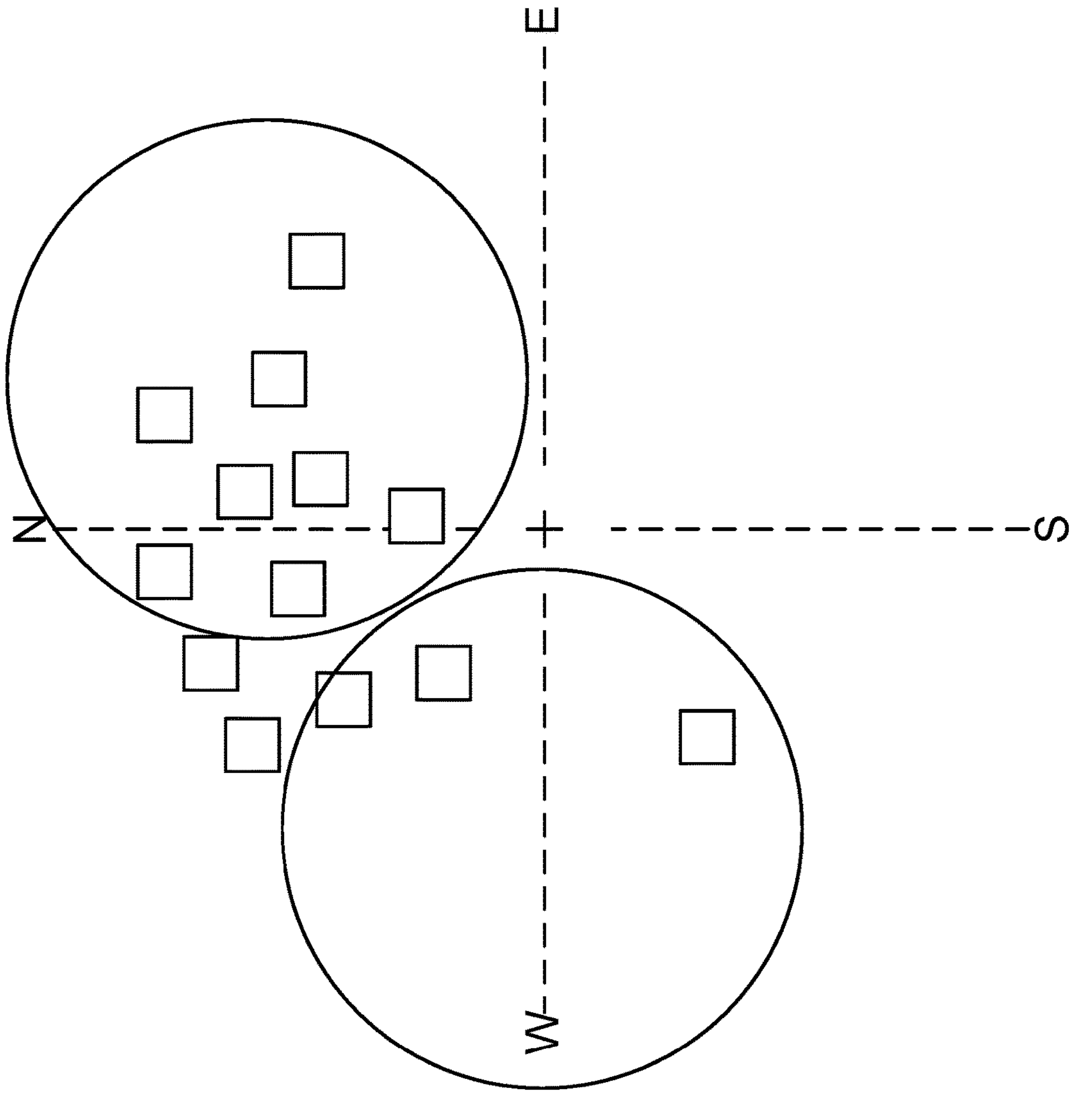
Figures 4, 8:
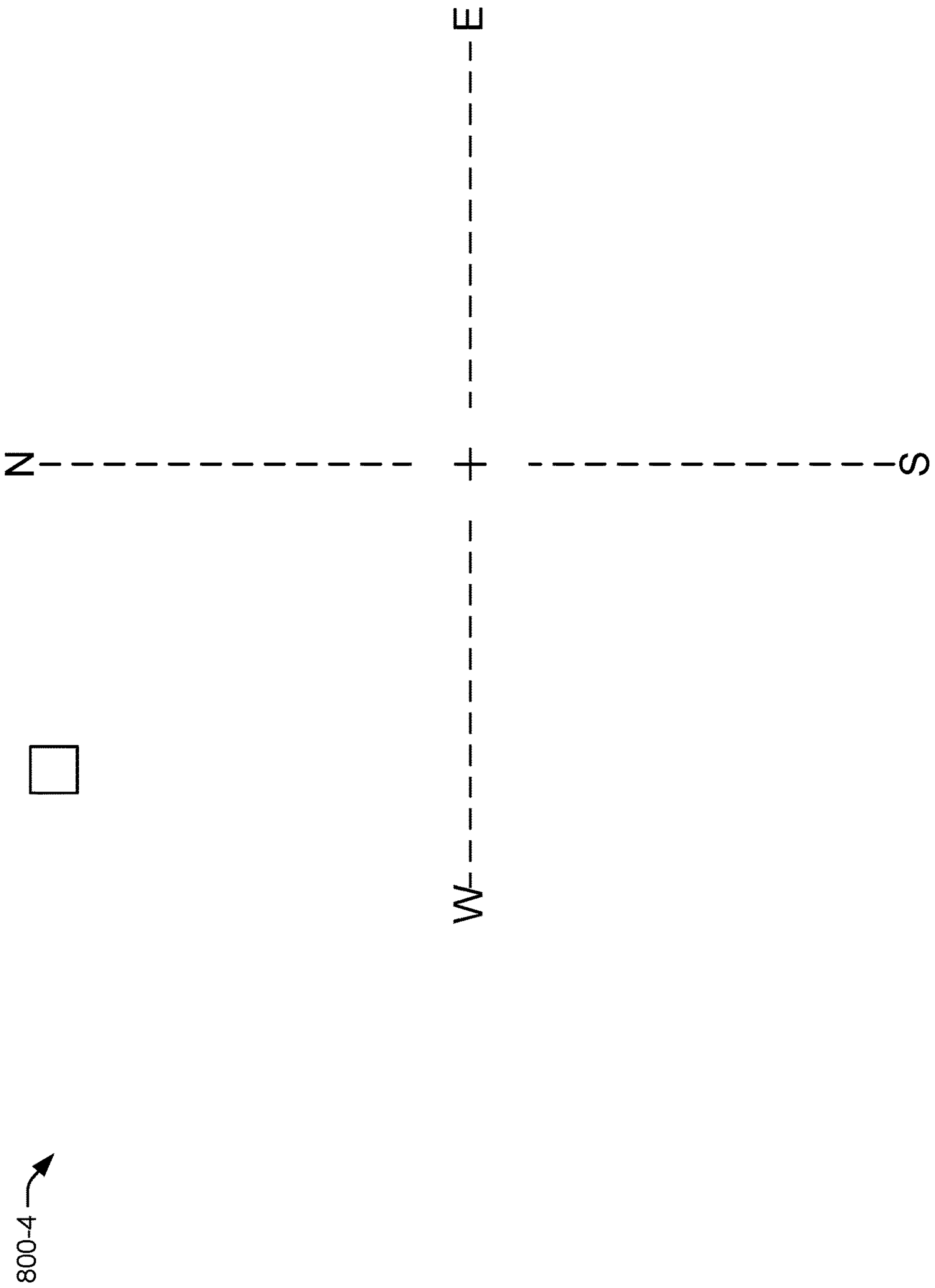

FIGS. 8-1 through 8-4 illustrate an example of containing a condition based on incidence maps generated by a computing system that maintains privacy during multi-modal on-device machine-learning. In FIG. 8-1, the ML models 116 of the user devices 102 have collected aggregated statistics about multiple subregions (white boxes) and reported those statistics to the map module 114 for plotting an incidence map 800-1. Because the incidence map 800-1 indicates where a condition is occurring, not where the condition is predicted to occur, containment operations (circles) are deployed around some of the subregions that are reported in the incidence map 800-2. In FIG. 8-3, the incidence map 800-3 is generated, showing different pockets of subregions and new containment operations (circles) are deployed around the other pockets. Finally, in FIG. 8-4, only a single subregion is shown affected by the condition. The containment or treatment operations were a success. Treatment occurred without ever exposing personal information about individual users or user devices.

The following are additional examples of the described systems and techniques for maintaining privacy for multi-modal on-device machine-learning and attribution of a condition.

Example 1. A computer-implemented method for maintaining privacy during attribution of a condition, the method comprising: training, by a remote system, a machine-learned model to infer, based on signals received by a user device in a geographic region, whether a person associated with the user device has the condition; deploying, by the remote system, copies of the machine-learned model for local execution at each of a group of user devices; collecting, by the remote system and from the group of user devices, aggregated statistics of inferences made by the copies of the machine-learned model; determining, by the remote system, based on the aggregated statistics, an incidence rate of the condition in a particular subregion of the geographic region; and outputting, by the remote system, based on the incidence rate of the condition in the particular subregion, an incidence map of the geographic region indicating a different incidence rate between multiple subregions of the geographic region.

Example 2. The method of example 1, wherein the condition comprises an infectious disease comprising malaria, chikungunya, zika, influenza, ebola, or dengue.

Example 3. The method of any one of examples 1 or 2, wherein training the machine-learned model comprises running the machine-learned model in inference mode based on ground truth data for the geographic region and the signals received by the user device in the geographic region.

Example 4. The method of any one of examples 1 through 3, wherein the copies of the machine-learned model are old copies of the machine-learned model, and training the machine-learned model to infer whether the person associated with the user device has the condition comprises: creating training data including examples of the signals received by the user device when the person associated with the user device has the condition and examples of the signals received by the user device when the person associated with the user device does not have the condition; retraining, based on the emulated training data, the machine-learned model; and generating new copies of the machine-learned model.

Example 5. The method of example 4, the method further comprising: deploying, by the remote system and to replace the old copies of the machine-learned model, the new copies of the machine-learned model for local execution at each of the group of user devices.

Example 6. The method of any one of examples 1 through 5, wherein collecting the aggregated statistics of inferences comprises: receiving a first portion of the aggregated statistics of inferences from a first user device of the group of user devices; inferring, based on the first portion of the aggregated statistics, a first subregion from the multiple subregions of the geographic region; attributing, based at least in part on the first portion of the aggregated statistics, a first rate of incidence of the condition to the first subregion; and generating the incidence map of the geographic region by indicating the first rate of incidence of the condition throughout the first subregion.

Example 7. The method of example 6, further comprising: receiving a second portion of the aggregated statistics from a second user device of the group of user devices, wherein: the first subregion from the multiple subregions of the geographic region is further inferred based on the second portion of the aggregated statistics; and the first rate of incidence of the condition is further attributed to the first subregion based on the second portion of the aggregated statistics.

Example 8. The method of any one of examples 6 or 7, further comprising: modeling, based on the aggregated statistics, a second rate of incidence of the condition for a second subregion from the multiple subregions; and generating the incidence map of the geographic region by further indicating the second rate of incidence of the condition throughout the second subregion.

Example 9. The method of example 8, wherein the group of user devices are located outside the second subregion at the time the inferences were made by the copies of the machine-learned model.

Example 10. The method of any one of examples 1 through 9, wherein the aggregated statistics of inferences made by the copies of the machine-learned model indicate presence or absence of the condition.

Example 11. The method of any one of examples 1 through 10, wherein the remote system comprises multiple remote systems.

Example 12. The method of any one of examples 1 through 11, wherein collecting the aggregated statistics of the inferences made by the copies of the machine-learned model is responsive to obtaining an indication of consent from a user of each user device from the group of user devices to collect the aggregated statistics.

Example 13. The method of any one of examples 1 through 12, wherein outputting the incidence map of the geographic region comprises outputting the incidence map to an application executing at a remote subscriber device.

Example 14. A computing system comprising at least one processor configured as the remote system to perform any one of the methods of examples 1 through 13.

Example 15. A computer-readable storage medium comprising instructions that, when executed, cause at least one processor of the remote system to perform any one of the methods of examples 1 through 13.

Example 16. A method for maintaining privacy supporting multi-modal on-device machine-learning and attribution of a condition for a geographic region, the method comprising: receiving, by a user device and from a remote system, a copy of a machine-learned model trained to infer, based on signals received by the user device while in a particular subregion of the geographic region, whether a person associated with the user device has the condition; inputting, to the machine-learned model, one or more of the signals received by the user device at two or more different intervals of time; responsive to inputting the one or more of the signals, determining a series of inferences made by the machine-learned model indicating in each inference whether the person associated with the user device has the condition; generating, by the user device, based on the series of inferences made by the machine-learned model, aggregated statistics as to whether people in the particular subregion have the condition; and outputting, to the remote system, an indication of the aggregated statistics to a remote system that generates an incidence map of the geographic region indicating a different incidence rate between multiple subregions of the geographic region including the particular subregion.

Example 17. The method of example 16, wherein the condition comprises an infectious disease comprising malaria, chikungunya, zika, influenza, ebola or dengue.

Example 18. The method of any one of examples 16 through 17, wherein generating the aggregated statistics comprises modifying the aggregated statistics by introducing noise.

Example 19. The method of example 18, further comprising: modifying a statistical sample of inferences in the series of inference to introduce noise in the aggregated statistics.

Example 20. The method of any one of examples 16 through 19, further comprising: generalizing the aggregated statistics to remove an identifier of the user or the user device prior to outputting the indication of the aggregated statistics to the remote system.

Example 21. The method of any one of examples 16 through 20, generalizing the aggregated statistics to remove an identifier of a particular location within the particular subregion prior to outputting the indication of the aggregated statistics to the remote system.

Example 22. The method of any one of examples 16 through 21, wherein signals received by the user device comprises signals obtained by a sensor of the user device.

Example 23. The method of any one of examples 16 through 22, wherein signals received by the user device comprises online data sent or received by the user device.

Example 24. The method of any one of examples 16 through 23, further comprising: executing an application that initiates the machine-learned model prior to the inputting.

Example 25. The method of example 24, further comprising: receiving an indication of the incidence map of the geographic region; and outputting, for display, a graphical user interface of the application including the incidence map.

Example 26. The method of example 25, wherein the aggregated statistics include initial statistics, the method further comprising: outputting, by the user device, to the remote system and based on subsequent inferences made by the machine-learned model, subsequent statistics as to whether people in the particular subregion have the condition; responsive to outputting the subsequent statistics, receiving an updated portion of the incidence map of the geographic region; and outputting, for display, an updated user interface of the application including the updated portion of the incidence map.

Example 27. The method of example 25, wherein the aggregated statistics include initial statistics, the method further comprising: receiving an updated portion of the incidence map of the geographic region having been updated by the remote system and based on subsequent statistics of inferences made by copies of the machine-learned model executing at other user devices as to whether people in particular subregions have the condition; and responsive to receiving the updated portion of the incidence map, outputting, for display, an updated user interface of the application including the updated portion of the incidence map.

Example 28. The method of any one of examples 16 through 27, wherein inputting the one or more of the signals received by the user device at two or more different intervals of time into the machine-learned model comprises conditioning the inputting on obtaining an indication of user input that consents to the machine-learned model inferring whether the user has the condition.

Example 29. A computing device comprising at least one processor configured as the user device to perform any one of the methods of examples 16 through 28.

Example 30. A computer-readable storage medium comprising instructions that, when executed, cause at least one processor of the user device to perform any one of the methods of examples 16 through 28.

While various embodiments of the disclosure are described in the foregoing description and shown in the drawings, it is to be distinctly understood that this disclosure is not limited thereto but may be variously embodied to practice within the scope of the following claims. From the foregoing description, it will be apparent that various changes may be made without departing from the spirit and scope of the disclosure as defined by the following claims.

What is claimed:

1. A computer-implemented method for maintaining privacy during attribution of a condition, the method comprising:

training, by a remote system, a machine-learned model to infer, based on signals received by a user device in a geographic region, whether a person associated with the user device has the condition, wherein the signals comprise daily routine signals and text-based signals associated with user devices, wherein the daily routine signals are based on location and mobility of user devices, wherein the signals further comprise indexed search information comprising search queries associated with the user device;

deploying, by the remote system, copies of the machine-learned model for local execution at each of a group of user devices;

for each individual machine-learned model of the copies of the machine-learned model, instructing a respective user device of the group of user devices to perform federated learning on a respective copy of the machine-learned model on the respective user device of the group of user devices;

collecting, by the remote system and from the group of user devices, aggregated statistics of inferences made by the copies of the machine-learned model;

determining, by the remote system, based on the aggregated statistics, an incidence rate of the condition in a particular subregion of the geographic region; and outputting, by the remote system, based on the incidence rate of the condition in the particular subregion, an incidence map of the geographic region indicating a different incidence rate between multiple subregions of the geographic region.

2. The method of claim 1, wherein the condition comprises an infectious disease comprising malaria, chikungunya, zika, influenza, ebola, or dengue.

3. The method of claim 1, wherein training the machine-learned model comprises running the machine-learned model in inference mode based on ground truth data for the geographic region and the signals received by the user device in the geographic region.

4. The method of claim 1, wherein the copies of the machine-learned model are old copies of the machine-learned model, and training the machine-learned model to infer whether the person associated with the user device has the condition comprises:

creating emulated training data including examples of the signals received by the user device when the person associated with the user device has the condition and examples of the signals received by the user device when the person associated with the user device does not have the condition;

retraining, based on the emulated training data, the machine-learned model; and generating new copies of the machine-learned model.

5. The method of claim 4, the method further comprising:

deploying, by the remote system and to replace the old copies of the machine-learned model, the new copies of the machine-learned model for local execution at each of the group of user devices.

6. The method of claim 1, wherein collecting the aggregated statistics of inferences comprises:

receiving a first portion of the aggregated statistics of inferences from a first user device of the group of user devices;

inferring, based on the first portion of the aggregated statistics, a first subregion from the multiple subregions of the geographic region;

attributing, based at least in part on the first portion of the aggregated statistics, a first rate of incidence of the condition to the first subregion; and generating the incidence map of the geographic region by indicating the first rate of incidence of the condition throughout the first subregion.

7. The method of claim 6, further comprising:

receiving a second portion of the aggregated statistics from a second user device of the group of user devices, wherein:

the first subregion from the multiple subregions of the geographic region is further inferred based on the second portion of the aggregated statistics; and the first rate of incidence of the condition is further attributed to the first subregion based on the second portion of the aggregated statistics.

8. The method of claim 6, further comprising:

modeling, based on the aggregated statistics, a second rate of incidence of the condition for a second subregion from the multiple subregions; and generating the incidence map of the geographic region by further indicating the second rate of incidence of the condition throughout the second subregion.

9. The method of claim 8, wherein the group of user devices are located outside the second subregion at the time the inferences were made by the copies of the machine-learned model.

10. The method of claim 1, wherein the aggregated statistics of inferences made by the copies of the machine-learned model indicate presence or absence of the condition.

11. The method of claim 1, wherein the remote system comprises multiple remote systems.

12. The method of claim 1, wherein collecting the aggregated statistics of the inferences made by the copies of the machine-learned model is responsive to obtaining an indication of consent from a user of each user device from the group of user devices to collect the aggregated statistics.

13. The method of claim 1, wherein outputting the incidence map of the geographic region comprises outputting the incidence map to an application executing at a remote subscriber device.

14. A computing system comprising at least one processor configured as a remote system to perform operations, the operations comprising:

training, by the remote system, a machine-learned model to infer, based on signals received by a user device in a geographic region, whether a person associated with the user device has a condition, wherein the signals comprise daily routine signals and text-based signals associated with user devices, wherein the daily routine signals are based on location and mobility of user devices, wherein the signals further comprise indexed search information comprising search queries associated with the user device;

deploying, by the remote system, copies of the machine-learned model for local execution at each of a group of user devices;

for each individual machine-learned model of the copies of the machine-learned model, instructing a respective user device of the group of user devices to perform federated learning on a respective copy of the machine-learned model on the respective user device of the group of user devices;

collecting, by the remote system and from the group of user devices, aggregated statistics of inferences made by the copies of the machine-learned model;

determining, by the remote system, based on the aggregated statistics, an incidence rate of the condition in a particular subregion of the geographic region; and outputting, by the remote system, based on the incidence rate of the condition in the particular subregion, an incidence map of the geographic region indicating a different incidence rate between multiple subregions of the geographic region.

15. A computer-implemented method for maintaining privacy during attribution of a condition, the method comprising:

receiving, by a user device and from a remote system, a copy of a machine-learned model trained to infer, based on signals received by the user device while in a particular subregion of a geographic region, whether a person associated with the user device has the condition;

performing federated learning on the copy of a machine-learned model on the user device;

inputting, to the machine-learned model, one or more of the signals received by the user device at two or more different intervals of time; responsive to inputting the one or more of the signals, determining a series of inferences made by the machine-learned model indicating in each inference whether the person associated with the user device has the condition, wherein the signals comprise daily routine signals and text-based signals associated with user devices, wherein the daily routine signals are based on location and mobility of user devices, wherein the signals further comprise indexed search information comprising search queries associated with the user device;

generating, by the user device, based on the series of inferences made by the machine-learned model, aggregated statistics as to whether people in the particular subregion have the condition; and outputting, to the remote system, an indication of the aggregated statistics to a remote system that generates an incidence map of the geographic region indicating a different incidence rate between multiple subregions of the geographic region including the particular subregion.

* * * * *